Figure 1A:
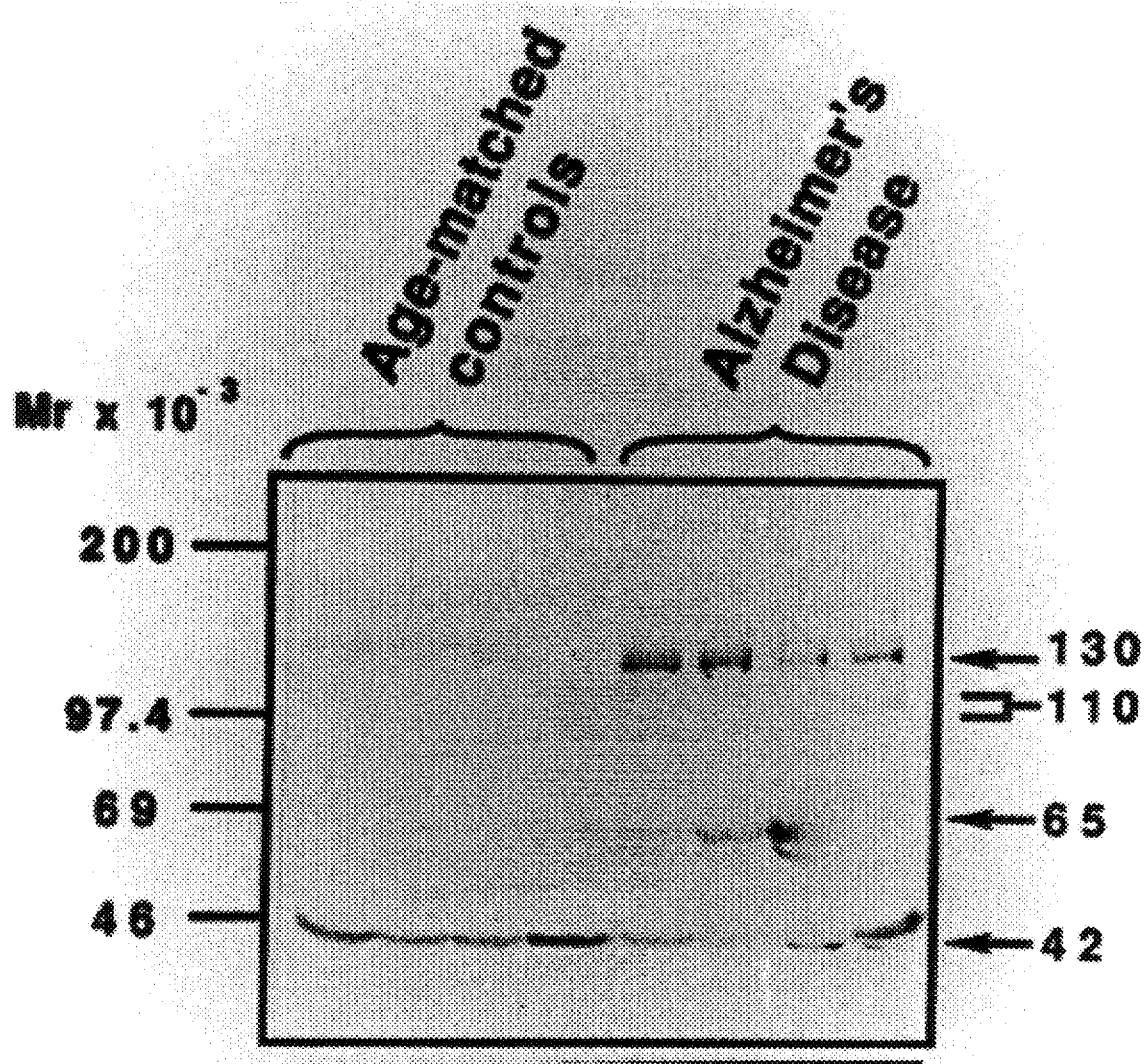

US005705401A

United States Patent [19]

Masters et al.

[11] Patent Number: 5,705,401
[45] Date of Patent: Jan. 6, 1998

[54] METHOD OF ASSAYING FOR ALZHEIMER'S DISEASE

[75] Inventors: Colin Louis Masters, Clifton Hill, Australia; Ashley Ian Bush, Boston, Mass.; Konrad Traugott Beyreuther, Heidelberg, Germany

[73] Assignee: The University of Melbourne, Victoria, Australia

[21] Appl. No.: 240,720

[22] PCT Filed: Nov. 12, 1992

[86] PCT No.: PCT/AU92/00610

§ 371 Date: Sep. 16, 1994

§ 102(e) Date: Sep. 16, 1994

[87] PCT Pub. No.: WO93/10459

PCT Pub. Date: May 27, 1993

[30] Foreign Application Priority Data

Nov. 12, 1991 [AU] Australia ............................ PK 9438
Jul. 8, 1992 [AU] Australia ............................ PL 3374

[51] Int. Cl.$^6$ ............... G01N 33/543; G01N 33/544; G01N 33/545
[52] U.S. Cl. .................... 436/518; 436/530; 436/531; 436/811
[58] Field of Search ................... 435/7.1, 7.94, 435/975; 436/811, 530, 531, 518; 530/350

[56] References Cited

U.S. PATENT DOCUMENTS 4,281,061  7/1981  Zuk et al. .......................... 435/7
5,234,814  8/1993  Card et al. ...................... 435/7.21

FOREIGN PATENT DOCUMENTS

| 33365/89 | 11/1989 | Australia . |
| 58173/90 | 1/1991 | Australia . |
| A04126095 | 4/1992 | Japan . |
| A04252954 | 9/1992 | Japan . |
| A04252955 | 9/1992 | Japan . |
| A04252956 | 9/1992 | Japan . |
| WO 91/16628 | 10/1991 | WIPO . |
| WO 92/00521 | 1/1992 | WIPO . |
| WO 92/13069 | 8/1992 | WIPO . |

OTHER PUBLICATIONS

Selkoe et al. (1988) "β-Amyloid precursor protein of Alzheimer disease occurs as 110-to 135-kilodalton membrane--associated proteins in neural and non-neural tissues". *Proc. Natl. Acad. Sci.*, 85:7341–7345.

Horns et al, Neurology 1989; 39:1159–1165 "The Consortum to Establish a Registry fo Alzheimer's Disease".

Bush et al, J. Biol. Chem, Sep. 15, 1990; 265(26):15977–15983 "The Amyloid Precursor Protein of Alzheimer's Disease is Released by Human Platelets".

*Primary Examiner*—Marian C. Knode
*Assistant Examiner*—Patricia A. Duffy
*Attorney, Agent, or Firm*—Scully, Scott, Murphy & Presser

[57] ABSTRACT

The present invention relates to a method of assaying for Alzheimer's disease in a human by determining the relative abundance of one or more forms of amyloid precursor protein (APP) or the enzyme responsible for said forms in circulatory fluid and to a method for treating the disease by modulating divalent cation, trivalent cation and/or heparin interaction with APP.

3 Claims, 10 Drawing Sheets

METHOD OF ASSAYING FOR ALZHEIMER'S DISEASE

The present invention relates to a method of assaying for Alzheimer's disease in a human by determining the relative abundance of one or more forms of amyloid precursor protein (APP) or the enzyme responsible for said forms in circulatory fluid and to a method for treating the disease by modulating divalent cation and/or heparin interaction with APP.

Alzheimer's disease is a progressive dementia characterised by the deposition of amyloid in the intracellular and extracellular compartments of the cerebral cortex (Davies et al, 1988). The extracellular deposits consist of a protein of 4,000 relative molecular mass ($M_r$=4K) referred to as βA4 (Kang et al, 1987). Molecular cloning and protein sequencing studies have shown that βA4 comprises part of the membrane spanning and extracellular domains of the amyloid precursor protein (APP), which has features of an integral transmembrane cell surface receptor (Kang et al, 1987; Goldgaber et al, 1987).

βA4 appears to result from abnormal cleavage of APP. Normal cleavage occurs at or near a lysine residue within the βA4 sequence (Esch et al 1990; Sisodia et al 1990; Palmert et al 1989). Cleavage at this site would prevent formation of the amyloidogenic βA4 fragment. The enzyme which normally cleaves APP from the membrane surface is designated "APP secretase" although it has never been identified.

At least one form of APP has been shown to have neurotrophic activity, i.e. capable of promoting the survival or outgrowth of nerve processes. A disorder in APP processing may account for the loss of certain populations of neurons seen in Alzheimer's disease. There is now increasing evidence that APP is released from membranes, as part of its normal neurotrophic function, by cleavage at a site within the βA4 sequence (lysine 16) by APP secretase. As βA4 is produced in Alzheimer's disease, this indicates that a failure to cleave at this site might be the cause of Alzheimer's disease or at least contribute to the profession of the disease.

There is a need for an assay which is of predictive and diagnostic value in monitoring Alzheimer's disease and for any therapeutic interventions therein. In accordance with the present invention, it has now been discovered that processing of circulatory. APP is altered in Alzheimer's disease thus providing a basis for an assay for the disease. Furthermore, from work leading up to the present assay, an improved means of treating Alzheimer's disease has been discovered based on modulating the interaction between divalent cations and/or heparin and APP.

Accordingly, one aspect of the present invention provides a method of assaying for Alzheimer's disease in a human said method comprising isolating a sample of circulatory fluid from said human, determining the amount of the 130 kDa form and/or 42 kDa form of APP and/or any derivatives of either form of APP in said fluid relative to a normal control wherein a relative increase in the 130 kDa form and/or its derivative and/or a relative decrease in the 42 kDa form and/or its derivative is indicative of the disease. By "assay" is meant screening or monitoring for the presence of, or a disposition to, Alzheimer's disease and/or to observe the effectiveness, or otherwise, of treatment of the disease following, for example, therapeutic intervention.

In accordance with the assay of the present invention, a sample of circulatory fluid is obtained from a test subject, generally after fasting since the prandial condition alters the level of APP in circulatory fluid, and the relative amounts of the 130 kDa and/or 42 kDa forms and/or their derivatives of APP determined. Fasting is generally for at least four hours but may be longer or shorter depending on the human to be tested. Fasting times may, for example, vary from 3 to 12 hours. Preferably, the circulatory fluid is blood plasma. A number of means exist for determining the relative amounts and such determination may be quantitative or qualitative. Conveniently, a Western blot is performed using an antibody, and preferably a monoclonal antibody, which recognises the amino terminal portion of APP. Mouse monoclonal antibody (MAb) 22C11 (Boehringer Mannheim, Munich, Germany) is one such antibody. Following a Western blot, a reflective analysis can then be conducted by computing the integrated reflectance (i.e. the area under the curve) for the peak corresponding to the 130 kDa and/or 42 kDa forms of APP and/or their derivatives.

One skilled in the art will immediately recognise that other forms of quantitation or qualitation are possible such as using HPLC and/or antibodies with different specificities to determine the relative levels of the different forms of APP. Such other methods are still within the scope of the present invention and include ELISA and competitive antibody assays. In any event, regardless of the means employed, it need only be determined that the 130 kDa form and/or its derivative of APP shows an increase and/or that the 42 kDa form and/or its derivative shows a decrease in their respective relative amounts to detect Alzheimer's disease and/or to monitor its progress.

The present invention also extends to genetic detection systems. These are of particular use in screening for people with a genetic predisposition to Alzheimer's disease. A genetic detection system, for example, may be based on a nucleic acid probe for the gene encoding the enzyme ("APPase") responsible for the alteration in circulatory APP.

According to this aspect of the present invention, there is provided a method of assaying for Alzheimer's disease in a human said method comprising isolating a sample of genetic material from said human, contacting said genetic material to an oligonucleotide capable of hybridising at or near the gene encoding APPase and ascertaining whether or not said APPase gene contains any nucleotide aberrations.

Preferably, the oligonucleotide is a probe and aberrations in the gene are determined by the extent of hybridisation to a region at or near said gene.

Alternatively, the oligonucleotide is a primer capable of directing amplification of DNA and aberrations are detected by sequencing of amplification products or measuring the profile of amplification products relative to a normal control.

In another embodiment, an antibody assay may be used to determine the amount of the enzyme. According to this embodiment there is provided a method for assaying for Alzheimer's disease in a human said method comprising isolating a sample of circulatory fluid from said human and contacting said fluid to a binding effective amount of an antibody specific to APPase and determining the amount of APPase in said fluid.

Preferably, the circulatory fluid is blood plasma.

Preferably, the antibody is a monoclonal antibody.

Conveniently, the binding of the antibody is determined by contacting the sample with a second antibody labelled with a reporter molecule and assaying a signed product by said reporter molecule.

In a specific embodiment the antibody is specific only for naturally occurring, active APPase.

By "derivative" means any single or multiple amino acid substitutions, deletions and/or additions to forms of APP occurring naturally or following direct or indirect therapeutic intervention. Accordingly, the present invention extends to monitoring the 130 kDa and/or 42 kDa forms or to any derivatives thereof which may possess higher or lower molecular weights. Hence, reference herein to the 130 kDa and 42 kDa forms of APP includes references to any derivatives thereof, where the relative amount of the derivative forms have the same or similar predictive and diagnostic value in monitoring Alzheimer's disease as the 130 kDa an 42 kDa forms.

In a most preferred embodiment, the present invention provides a method for assaying for Alzheimer's disease in a patient, said method comprising isolating plasma from said patient and subjecting same to partial purification, identifying the 130 kDa and/or 42 kDa forms and/or their derivatives of APP in said partially purified plasma preparation by suitable means such as Western blot analysis using an antibody to the amino terminal portion of APP and then determining the amounts of said 130 kDa and/or 42 kDa forms and/or their derivatives relative to normal controls. By "partial purification" is meant that required to reduce interference by non-APP proteins and other molecules during the detection, such as by Western blot analysis. Conveniently, the partial purification is conducted by collecting the plasma in heparinised collection tubes, obtaining the plasma supernatant and subjecting same to heparin-Sepharose chromatography.

The present invention also relates to antibodies to the 130 kDa and/or 42 kDa forms and/or their derivatives of APP and to antibodies to APPase. The antibodies may be polyclonal or monoclonal antibodies or may be recombinant or chemically synthetic forms thereof. Such antibodies will be useful inter alia in the detection assay of the present invention. In this regard, these antibodies may be labelled with a reporter molecule such as an enzyme, radioisotope, chemiluminescent molecule, fluorescent molecule and the like. Alternatively, a labelled second antibody, specific to the first antibody, could be employed. The present invention, therefore, extends to the second antibody, whether or not the antibody is labelled. The said second antibody may be polyclonal monoclonal or synthetic as with the first antibody.

Yet a further aspect of the present invention provides a kit for assaying for Alzheimer's disease in a human said kit comprising in compartmental form a first compartment adapted to contain an antibody specific to the 130 kDa form and/or the 42 kDa form and/or derivatives thereof or to APPase; and optionally a second compartment adapted to contain a second antibody specific to said first antibody and labelled with a reporter molecule. The kit may also further comprise means for conducting a Western blot and/or some other quantitative or qualitative detection means. The kit may yet further comprise means for partially purifying the 130 kDa and/or 42 kDa forms and/or their derivatives of APP and/or APPase from the circulatory fluid such as plasma.

In yet another aspect of the present invention, there is provided a method for treating Alzheimer's disease in a patient in need thereof comprising subjecting said patient to means for modulating divalent cation and/or trivalent cation and/or heparin interaction with APP. Preferably, zinc interaction or heparin or any other moiety that binds to the heparin binding site with APP is modulated. This aspect of the present invention is predicated in part on the discovery that by manipulating the interaction between .cations, preferably zinc, and APP, protease mediated digestion of APP (i.e. APPase activity) is altered.

An elevation in APP levels occurs in Alzheimer's disease. Elevations of APP mRNA are known to occur in the brains of sporadic Alzheimer's disease cases and are the most likely the pathogenetic event in the amyloidogenesis that invariably accompanies Down's Syndrome. Increases in APP levels can be induced in normal and Alzheimer's disease volunteers, in rats and in PC12 cultured cells by extracellular zinc loading. It is demonstrated herein that extracellular zinc modulates APP expression. This provides a basis for therapeutic intervention based on modulating divalent cation interaction with APP.

By modulating the levels of divalent cations or heparin or any other moiety which can bind the heparin binding sites on APP (residues 318–331 and around residues 93–105) or any other binding site on APP capable of binding these moieties (such as additional zinc or heparin binding sites on APP), the range, type and/or extent of APP cleavage can be altered such that incorrect protease-mediated processing of APP can be reduced or inhibited. By "modulate" is meant the alteration of the availability of divalent cations and trivalent cations or heparin or any other moiety which can bind the heparin binding sites on APP (residues 318–331 and around residues 98–105) or any other binding site on ATP capable of binding these moieties (such as additional zinc or haparin binding sites on APP) to bind to APP prior to or simultaneously with APPase-mediated cleavage. It has been found that zinc ($Zn^{2+}$) binds to APP at a specific and saturable binding site. The zinc binding site on APP was identified by enzymatic digestion of purified APP695-fusion protein coupled to $Zn^{2+}$-chelating sepharose. The synthetic peptide representing about residues 181–200 of APP, situated between the cysteine rich and negatively charged domains of the protein, was shown to bind zinc in a specific and saturable manner. The intimate involvement between APP and zinc is strongly suggestive of a role of zinc in APP processing: APP binds heparin (in a manner analogous to FGF). Heparin has been shown to protect APP from proteolytic digesion, as exemplified using the proteolytic enzyme trypsin. Heparin concentration as low as 100 nM cause a marked reduction in the rate and degree of brain APP degradation by trypsin. The brain contains a number of heparin or heparin sulphate containing proteins and thus the interaction of heparin with APP may stabilise APP from proteolytic degradation in-vivo. It has also been found that zinc effects the kinetics of heparin binding to APP, and may increase APP affinity for heparin 5 to 10 fold. Surprisingly, at low zinc concentrations (above about 1 μm) the protective effects of heparin are abolished. This finding indicates that aberrant zinc levels in-vivo, in the brain intracellular and/or extracellular millieu, may promote aberrant APP proteolytic processing giving rise to the amyloid protein, and subsequently Alzheimer's disease and other disorders associated with amyloid deposition in the brain.

The mechanisms behind zinc abolishing the protective effects of heparin are uncertain.

Studies conducted in Alzheimer's disease patients demonstrate that administration of zinc (such as elemental zinc in the form of sulphate) at a moderate oral dosage such as 50 to 100 mg of grams per day over several days (in keeping with conventional zinc supplements obtainable from pharmacies) leads to rapid deterioration of neural functioning as demonstrated by a severe loss of cognitive function with mini-mental state examination (Folstein et al., 1975) scores deteriorating from moderately demented levels to unrecordable. Eye movement abnormalities and general levels of self care worsened over the period of supplementation. In contrast, healthy volunteers showed no ill effects from zinc supplementation.

The results obtained from Alzheimer's patients is consistent with a neurotoxic response to zinc metabolism in the brain in Alzheimer's disease.

In one aspect of this invention Alzheimer's disease and other neurological disorders are treated, ameliorated and/or prevented by administering to a patient in need of such treatment a therapeutically effective amount of a zinc binding agent which agent is capable of binding a divalent or trivalent cation and thereby modulating its interaction with APP. More particularly, the cation is a divalent cation and even more particularly is zinc and the binding agent is a zinc binding agent. This modulation may comprise reducing the bioavailability of zinc due to the formation of complexes with zinc thus reducing free zinc. Zinc binding may, for example, take place in the gastrointestinal tract, in the blood stream and/or in the brain, such as at an extracellular and/or intracellular level.

Any pharmaceutically acceptable zinc binding agent may be employed in this invention. Particularly preferred are binding agents which are capable of crossing the blood/brain barrier and thus modulate free zinc concentrations within the brain at an extracellular and/or intracellular level in order to restore aberrant zinc levels in the brain thus protecting against improper APP processing which may give rise the amyloid protein. Examples of zinc binding agents (such as chemical chelators) include phytic acid and derivatives thereof (such as phytate), desferrioxamine, sodium citrate, ethylene diamine tetra acetic acid (EDTA), and zinc specific chelating agents based on heterocyclic pyridones such as 1,2-diethyl-3-hydroxypyridin-4-one (CP94) and 1-hydroxyethyl-3-hydroxy-2-methylpyridin-4-one (CP40) (Hilder et al., 1990), which agents may be capable of crossing cell membranes (CP94) or incapable of permeating cells (CP40).

Zinc interaction with APP may be modulated by diet, by administering to patients a low zinc diet, or removing dietry sources of zinc. Zinc is enriched in numerous foodstuffs. Prominent amongst these are oysters, crab, beef, liver and other seafood and animal products (Stanton, 1992). The bioavailability of zinc is inhibited by unprocessed wheat bran, high alcohol and various proteins. Avoidance of animal products combined with a diet containing unprocessed fibre, such as wheat bran, may reduce the bioavailability of zinc and hence reduce the contribution of zinc to neurotoxicity. Thus, in accordance with this aspect there is provided a method for treating/ameliorating or preventing Alzheimer's disease which comprises administering to a subject in need of such treatment a diet low in free zinc.

The term "modulate" extends to the use of pharmacological agents which disrupt zinc transport mechanisms across cell membranes. Like other metal ions, such as iron and calcium, zinc is transported into cells via a zinc transport system (currently poorly characterised) which may involve one or more proteins and/or lipids and/or carbohydrates which regulates zinc flow across membranes. Pharmacological agents which disrupt one or more components of the zinc transport system may be used to block zinc uptake from the intestines as well as zinc transport into and out of cells in the brain. Accordingly, there is provided in this aspect a method for modulating zinc interaction with APP which comprises administering to a subject a pharmacological agent capable of blocking one or more components of the zinc transport system so as to reduce zinc uptake. Using such agents it may be possible to correct the maldistribution of zinc in extracellular and intracellular compartments in Alzheimer's disease. The term "modulate" further extends to means for affecting the interaction of the cations to APP. Such means include, for example, changes in pH. "Modulate" also extends to altering zinc metabolism with agents such as iron supplements which, for example, suppress zinc absorption from the gut and promote zinc elimination, or by blocking the cation binding site on APP or on the cation responsive promoter region of the APP gene, for example with cupric ions.

Administration of zinc .binding compounds and pharmacological agents capable of disrupting the zinc transport system may be by parenteral or oral administration although all other known modes of administration are contemplated by the present invention.

Sustained high concentrations of extracellular zinc (greater than 200 µM) are known to be neurotoxic. Zinc concentrations in hippocampal synapes briefly reach 300 µM during synaptic transmission. The disruption of extracellular zinc metabolism may be an important step in the neurotoxic mechanism that accompanies amyloid deposition in Alzheimer's disease. The findings disclosed herein support the proposition that APP is important in the regulation of neuronal zinc compartmentalisation. An abnormality of APP metabolism may consequently cause an abnormality of zinc metabolism. A strategy to remedy this abnormality in Alzheimer's disease would involve the restoration of normal APP metabolism, for example by reversing the abnormal APP protease resistivity that occurs in Alzheimer's disease, or by treating the Alzheimer's disease patient with supplements of normal APP.

It is to be understood that aspects of this invention involving modulation of zinc levels run counter to previously proposed therapies which suggested Alzheimer's disease may be associated with zinc deficiencies and thus proposed administering zinc to patients suffering from Alzheimer's disease. As described herein it has been found that administration of zinc to Alzheimer's disease patients worsens the disease, this being evaluated by standard neurological testing.

It has surprisingly been found that Alzheimer's disease may be detected by administering to a subject a challenge of zinc, and thereafter testing neurological function according to one or more standard tests as are well known in the art. When compared to non-Alzheimer's normal controls, a person suffering from Alzheimer's disease shows a decrease in cognitive abilities as well as a decrease in other standard neurological function tests. One convenient test is an assessment of eye movement to visual stimuli which is reduced markedly in Alzheimer's disease patients on zinc challenge compared to normal controls. The mount of zinc administered to a subject in a challenge test would generally comprise from 50 to 500 mg or more. The precise amount of zinc administered in a test is not crucial and would generally be based on minimising side effects to zinc administration in Alzheimer's patients.

Thus, in a further aspect of this invention there is provided a method for detecting Alzheimer's disease which comprises administering to a subject a challenge of zinc and thereafter assessing neurological function, where a decrease in neurological function compared relative to normal controls is indicative of Alzheimer's disease.

The zinc challenge may be administered to a patient in various ways, such as orally, intravenously, intramuscularly, transdermally, rectally, intranasally and the like. Oral administration is preferred. As mentioned above, the mount of zinc administered to a patient in a challenge test is not critical as long as the mount administered is capable of evoking a response in Alzheimer's patients without precipitating severe disease symptoms.

The present invention is further described by reference to the following non-limiting figures and examples.

Figure 1B:
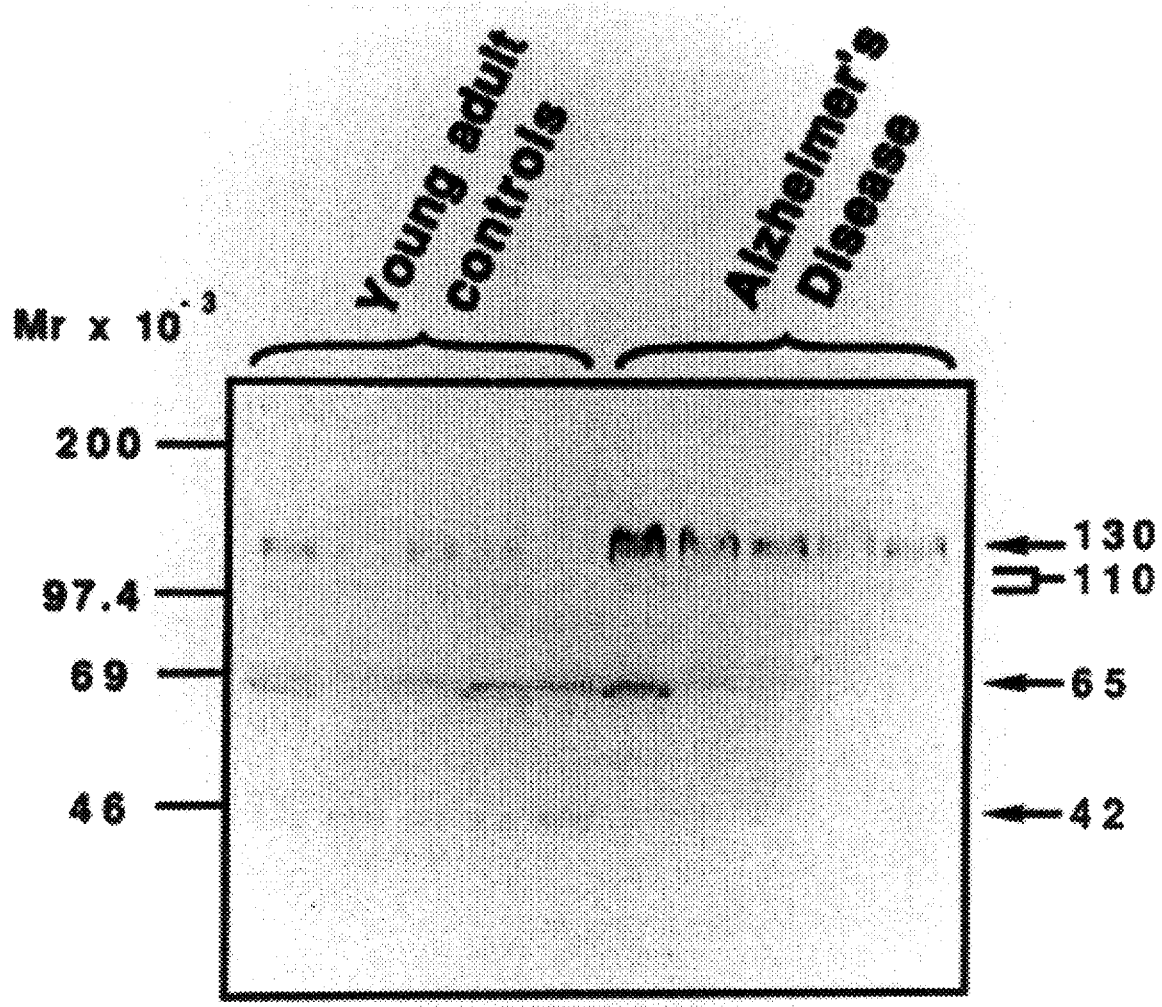

In the Figures:

FIGS. 1A and 1B are a photographic representations showing immunoblots comparing Alzheimer's disease and age matched control plasma APP. Plasma heparin-Sepharose eluates (65 μg) were analysed by 8.5% (w/v) SDS polyacrylamide gel electrophoresis and immunoblotting with MAb 22C11 which recognises an amino-terminal epitope (see Example 1). The relative molecular mass of standard protein markers (Rainbow Standards, Amersham, UK) are shown on the left. APP immunoreactive bands of 130, 110 (a doublet), 65 and 42 kDa are indicated by arrows to the right. Only the relative abundances of the 130 and 42 kDa APP forms, as in the sample illustrated, could visibly discriminate between Alzheimer's disease compared to (FIG. 1A) non-demented elderly controls and (FIG. 1B) normal young control populations.

Figure 2:
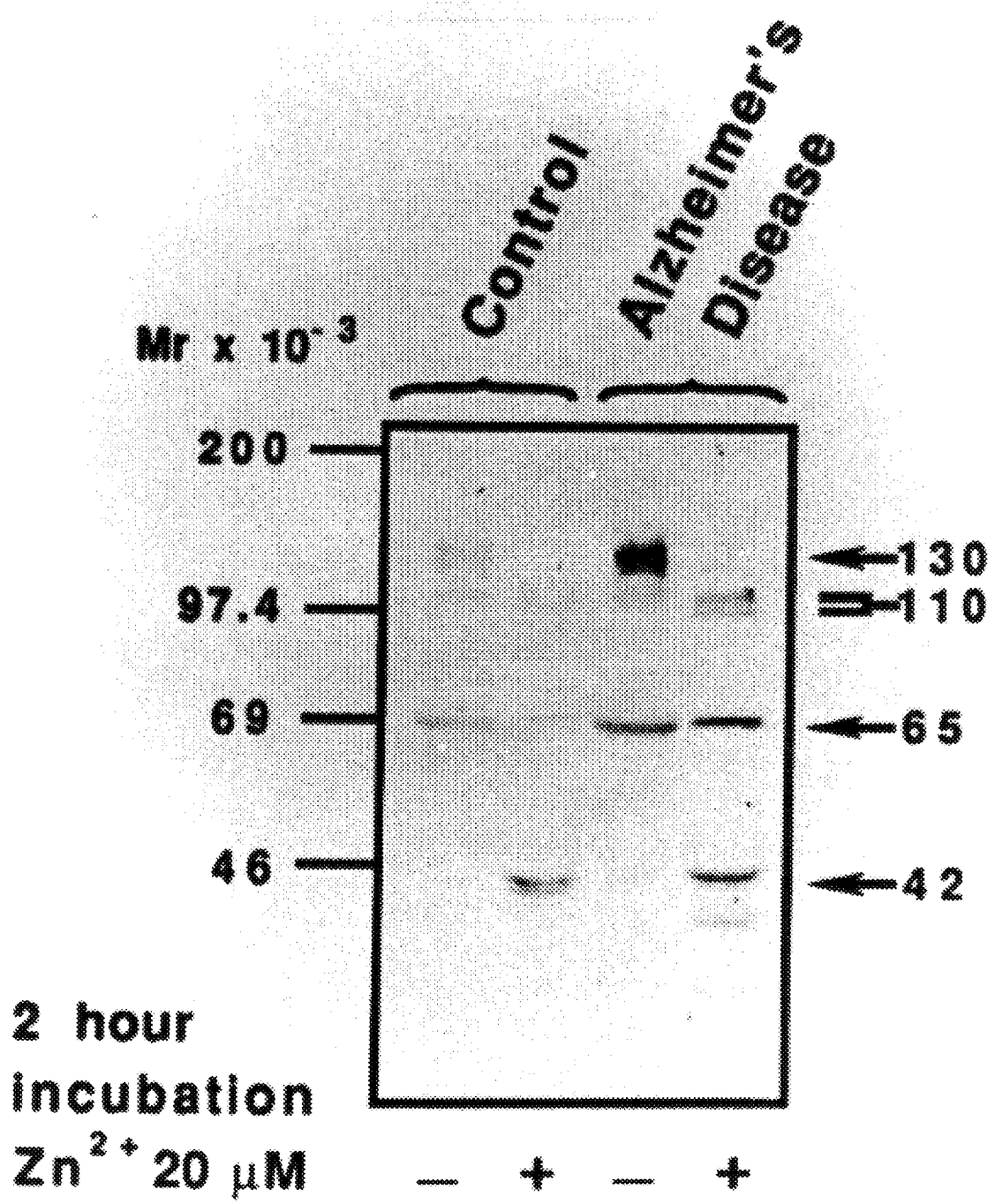

FIG. 2 is a photographic representation showing a comparison of APP proteolytic activity from Alzheimer's disease (B) and control plasma (A). Heparin-Sepharose purified APP from plasma of Alzheimer's disease and control cases were incubated for 2 hours at 37° C. in saline buffer in the presence or absence of 20 μM $Zn^{2+}$. Samples (65 μg of protein) of each incubation were analysed by electrophoresis on 8.5% (w/v) polyacrylamide gels and immunoblotted with 22C11. The relative molecular mass of standard protein markers (Rainbow Standards, Amersham, UK) are shown on the left. APP immunoreactive bands of 130, 110, 65 and 42 kDa are indicated by arrows on the right. The figure shows samples representative of six Alzheimer's disease cases and six normal young adult controls.

Figure 3:
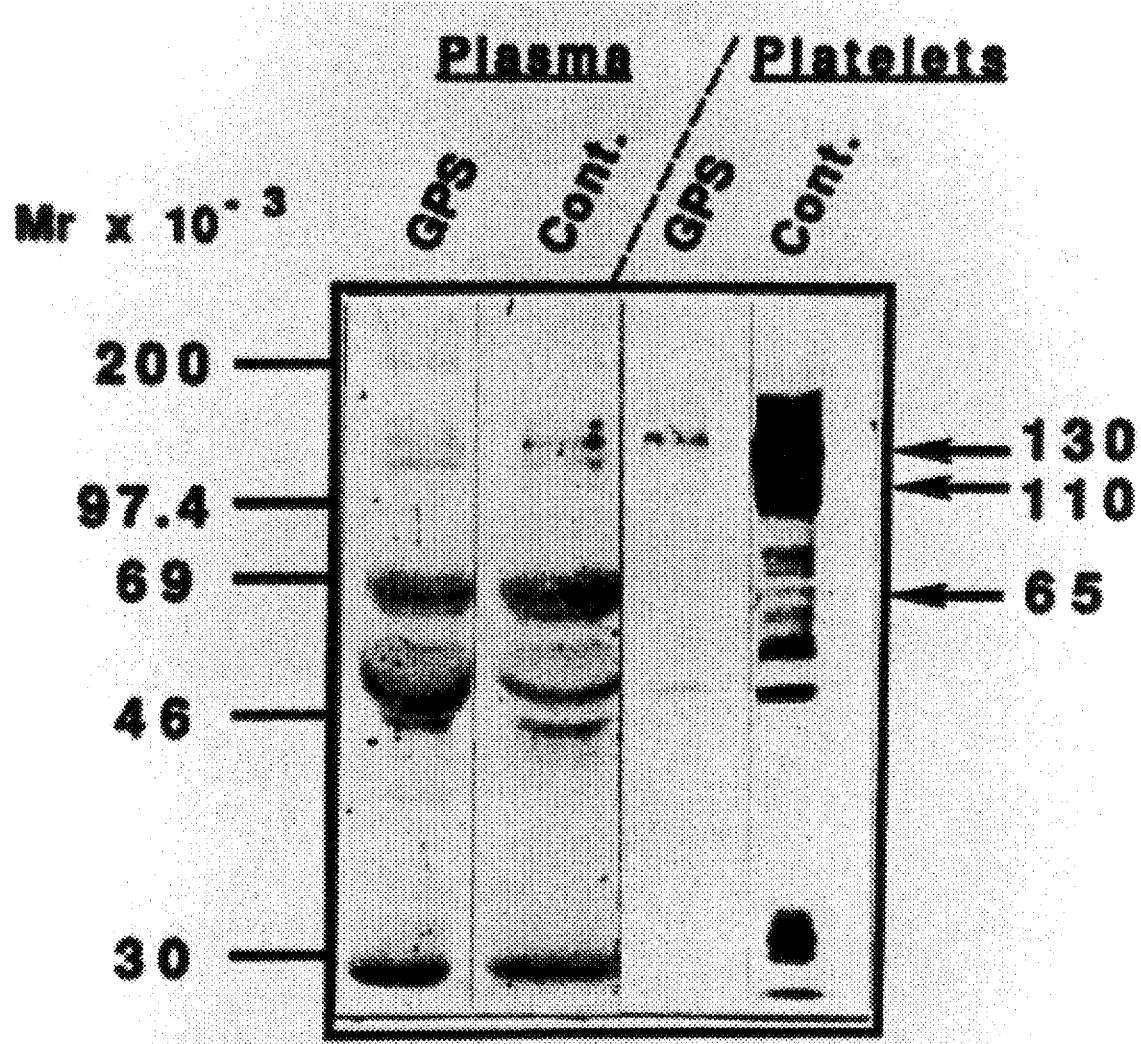

FIG. 3 is a photographic representation of a Western blot of platelets and plasma from gray platelet syndrome compared to control. An aliquot of 65 μg of plasma purified by heparin-Sepharose chromatography and 50 μg of washed whole platelets from a patient with gray platelet syndromes (GPS) were compared to similar preparations obtained from a young adult control. The samples were analysed by 10% (w/v) polyacrylamide mini-gel electrophoresis and immunoblotted with 22C11. The relative molecular mass of standard protein markers (Rainbow Standards, Amersham, UK) are shown on the left. The positions of major immunoreactive bands in normal platelets (130 and 110 kDa) and a minor band (65 kDa) are indicated by arrows on the right.

Figure 4:
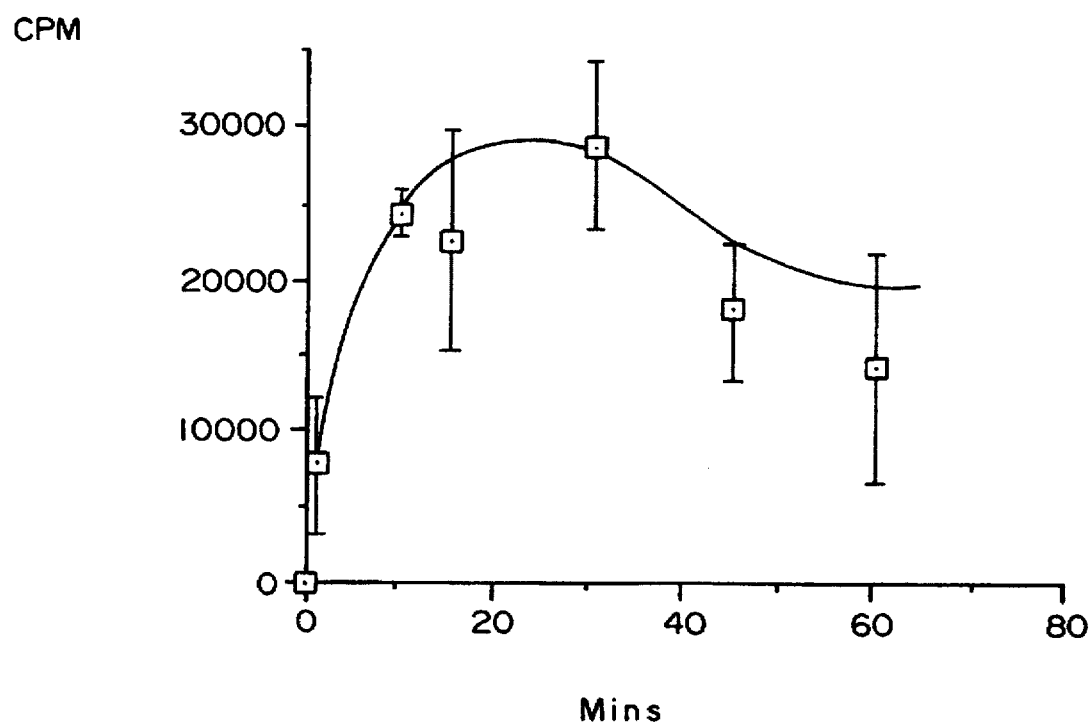

FIG. 4 is a graphical representation showing a time course analysis of $^{65}Zn$ binding to human brain 130/110 kDa APP. Amyloid protein precursor (APP) was purified according to the method in Moir et al (1992). The preparation of purified 130 and 110 kDa APP was derived from human brain membrane extracts and contained the full-length precursor with carboxyl terminus intact but lacked the 17 residue signal peptide. The 130 and 110 kDa proteins were apparent in equal ratios on silver staining following polyacrylamide gel electrophoresis and were the only bands visible. The identity of these two proteins was confirmed by Western blots with monoclonal antibody 22C11 (which recognises an amino terminal epitope on APP), and by amino terminal sequencing. The protein concentration of the APP preparation was determined by amino acid analysis. Aliquots of APP (90 ng,≈1.1 pmole, assuming the average amino acid formula weight of APP is≈80 kDa) were incubated at 20° C. for the times indicated. Incubations (50 μ) were performed in 150 mM NaCl, 50mM Tris-Hcl, pH 7.4 in the presence of $10^6$ cpm of $^{65}Zn$ (175 nM). The incubation solution was then applied to a 1.1 ml bed volume Sephadex G25 (Pharmacia, Uppsala, Sweden) column pre-equilibrated with 150mM NaCl, 50 mM Tris-HCl, pH 7.4 and allowed to settle before being desalted with 645 μl of the Equilibration buffer. Previous analysis of the desalting properties of the column with mixtures of Dextran Blue and potassium dichromate solution indicated that >95% of the protein in the incubation mixture would be desalted into this volume with no detectable free salt present. The desalted protein was collected directly into counting tubes containing 10 ml aqueous counting scintillant. Less than two minutes was required to complete the desalting. The amount of $^{65}Zn$ bound to desalted APP was determined by counting the collected sample in a beta-counter set to the broadest channel. Counting was determined to be 51% efficient. The values shown are means±SD of n≥3 readings. These data indicate that rapid binding of Zn to APP occurs (≈30% of Bmax at 5 minutes) and reaches a maximum at 30 mins.

Figure 5:
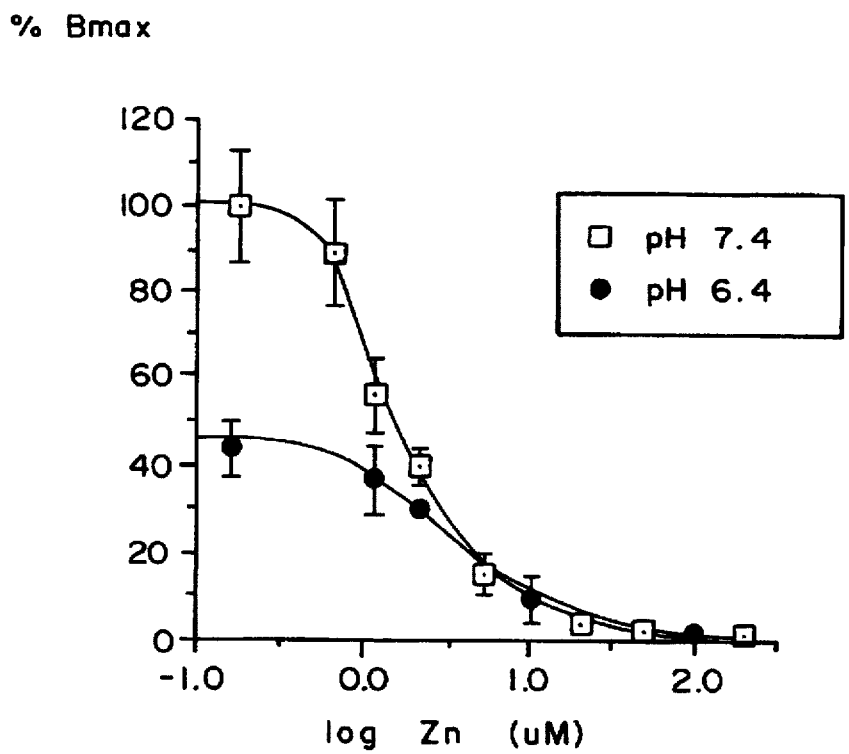

FIG. 5 is a graphical representation showing a competition analysis of $^{65}Zn$ binding to human brain 130/110 kDa APP. Aliquots of APP were incubated for 30 minutes with $^{65}Zn$ as in FIG. 4. The binding of the labelled $Zn^{2+}$ to APP was subjected to competition with unlabelled $Zn^{2+}$ in the form of the chloride salt. Data shown indicate the competition curves generated at pH 6.4 and 7.4. The binding of $Zn^{2+}$ to APP deteriorated at the lower pH (≈45% of Bmax, pH 7.4). The values are means±SEM of n≥3 readings. The curves illustrated are typical of three experiments.

Figure 6:
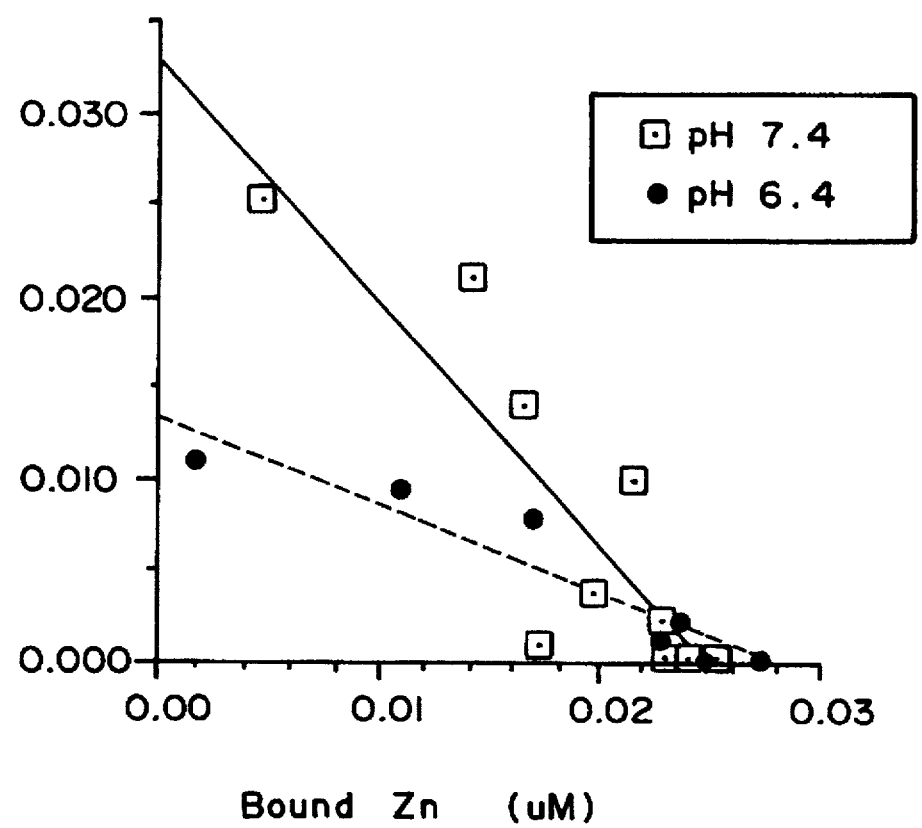

FIG. 6 is a graphical representation depicting a Scatchard analysis of $^{65}Zn$ binding to human brain 130/110 kDa APP. Derived from the data points in FIG. 5, Scatchard analysis reveals that the dissociation constant ($K_D$) for the $Zn^{2+}$ binding site on APP is 764 nM at pH 7.4 and 2.08 μM at pH 6.4. One APP molecule binds one zinc ion.

Figure 7A:
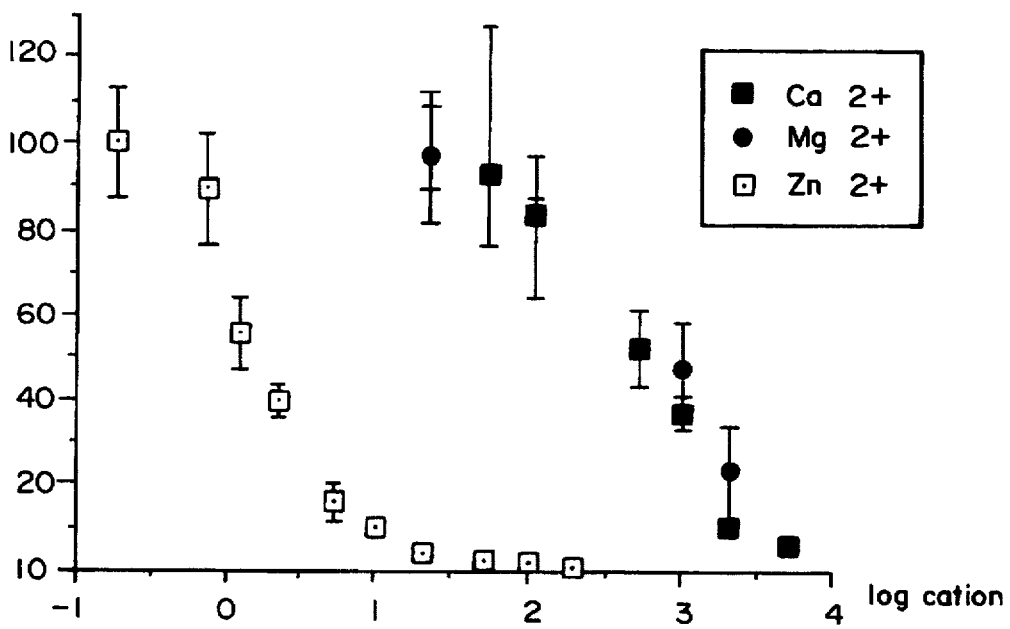
Figure 7B:
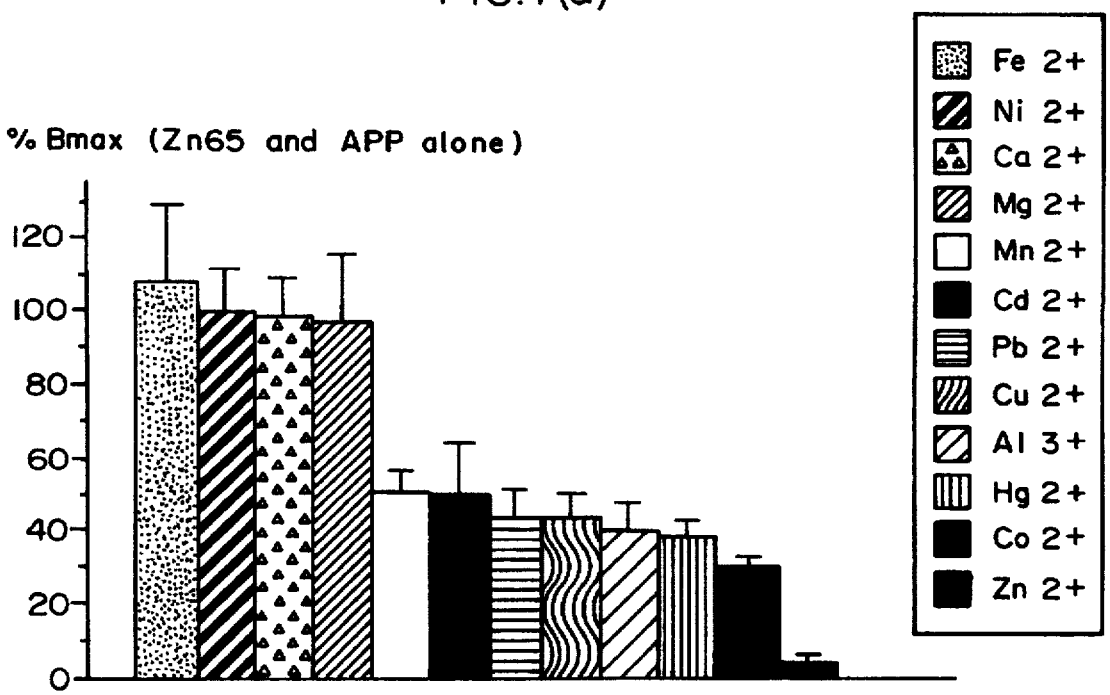

FIGS. 7A and 7B are a graphical analyses showing a specificity study of the $Zn^{2+}$ binding site on APP.

(a) APP incubation with $^{65}Zn$ and competing unlabelled $Zn^{2+}$ was performed under the conditions detailed in FIG. 5. In addition, the effect of competition for $Zn^+$ binding by $Ca^{2+}$ and $Mg^{2+}$ is shown. The values are means±SEM of n≥3 readings. The competition curves for $Ca^{2+}$ and $Mg^{2+}$ are shifted greater than two log units to the right of the $Zn^{2+}$ competition curve, indicating that the binding site is more specific for $Zn^{2+}$ at physiological concentrations.

(b) Comparison was made of the ability of other metal ions to compete with $^{65}Zn$ for binding to APP. APP incubations with $^{65}Zn$ and competing unlabelled metal ions (at 20 μM) were performed under the conditions detailed in FIG. 5. The values are means±SEM of n≥3 readings. $Zn^{2+}$ could compete>97% of the label off the APP at 20 μM. $Co^{2+}$ was the next most competitive metal ion, competing≈70% of the label off the APP at the same concentration.

Figure 8:
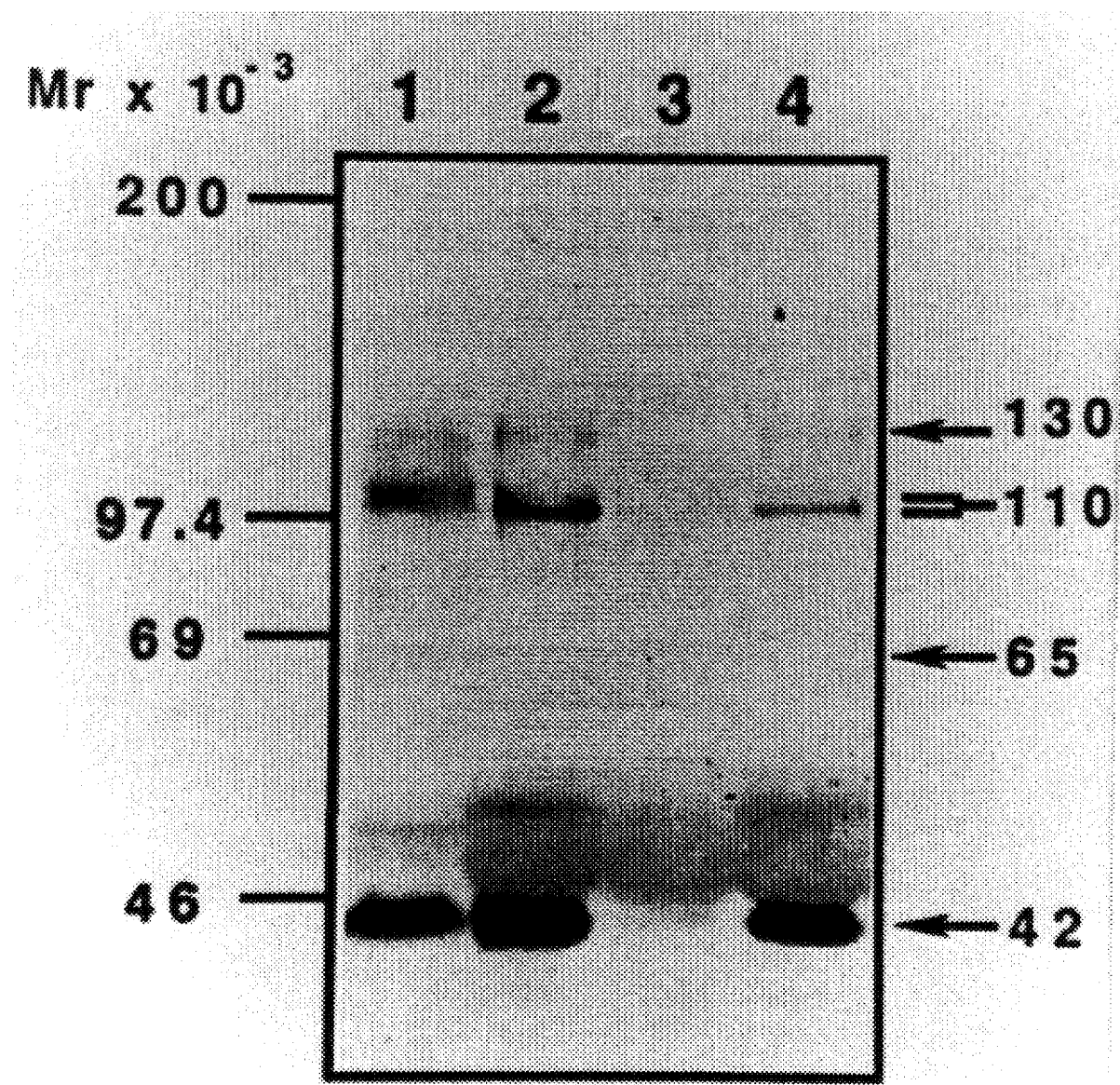

FIG. 8 is a photographic representation showing an analysis of immunoreactive APP in plasma by western blot. APP immunoreactive proteins in heparin-Sepharose eluates from plasma were analysed by 8.5% SDS polyacrylamide gel electrophoresis and western blotting with mAb 22C11. Lane 1: Heparin-Sepharose eluate of plasma (65 μg of protein). Lane 2: Heparin-Sepharose eluate immunoprecipitated by antiserum 90/3 (raised against full-length human brain APP). Lane 3: Heparin-Sepharose eluate immunoprecipitated by the prebleed to antiserum 90/3. Lane 4: Heparin-Sepharose eluate immunoprecipitated by anti-Fd-APP (raised against APP fusion protein). The relative molecular masses of standard protein markers (Rainbow Standards, Amersham, UK) are shown on the left. APP immunoreactive bands previously reported[15] of 130, 110 (a doublet), 65 and 42 kDa, are indicated by arrows on the right.

Figure 9A:
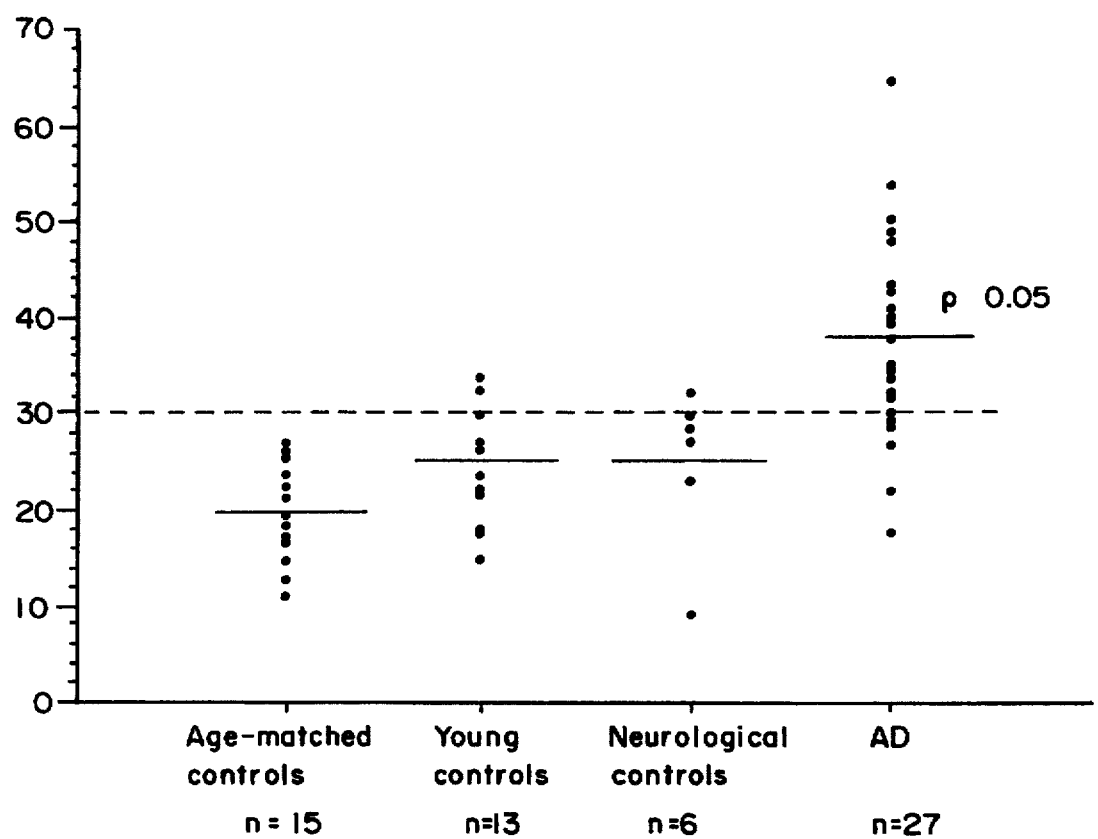
Figure 9B:
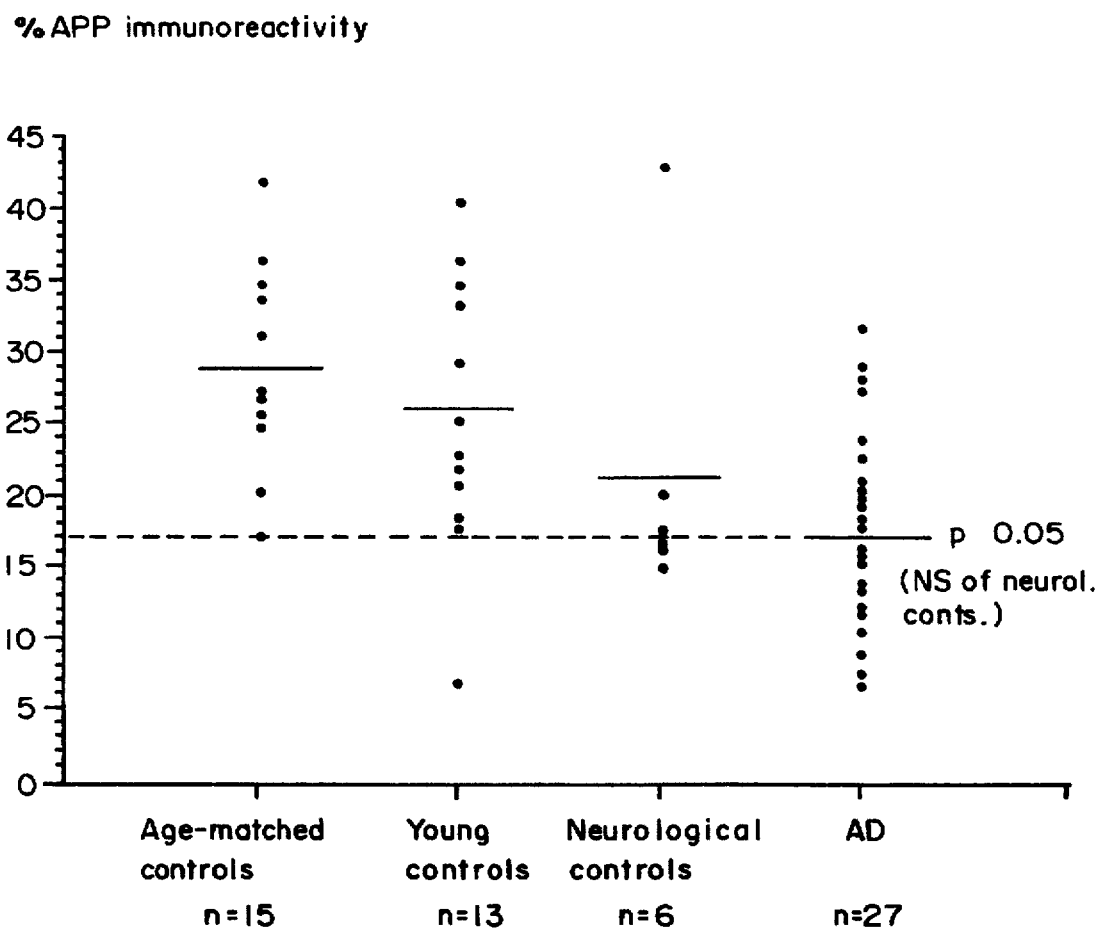

FIGS. 9A and 9B are a graphical representations of scattergrams of reflectance analysis of immunoblots comparing AD and control plasma APP. The distribution of plasma APP immunoreactivity was analysed by reflectance as detailed in Table 1. Solid lines indicate the means for each subgroup. A significant difference in the levels of 130 and 42 kDa species of APP was seen between AD and pooled control groups. Therefore, further analysis was performed on the differences in the concentrations of these species between these groups. (a) Proportions of 130 kDa APP in the AD group and individual control groups. The means proportion of 130 kDa APP species ranged approximately 50% to 80% ($p \leq 0.05$; Scheffé, 1959) greater than the AD group compared to each control group. The dotted line indicates a suggested threshold for a biochemical characterization of AD providing 91% specificity and 78% sensitivity. (b) Proportions of 42 kDa APP concentrations in the AD group compared to the individual control groups. The mean proportion of the 42 kDa APP species ranged approximately 30% to 40% ($p \leq 0.05$; Scheffé, 1959) lower in the AD group compared to the young adult and the age-matched control groups. The dotted line indicates a threshold for a biochemical characterization of AD providing 85% specificity and 50% sensitivity.

EXAMPLE 1

Materials and Methods

Materials:

All reagents were analytical grade except for the Tris-HCl which was electrophoresis grade (BioRad) to avoid contamination with traces of zinc. $^{65}Zn$ was purchased from Amersham (U.K.).

Case selection:

Alzheimer's disease cases met NINCDS/Alzheimer's diseaseRDA clinical criteria (McKann et al, 1984) and had Mini-menial state (Folstein et al, 1975) scores of less than 17. Age-matched controls each underwent a Mini-mental state examination and were excluded if they scored less than 28. The different neurological diagnoses used as non-demented neurological disease controls (n:=6) were epilepsy, demyelinating disease, hydrocephalus and three cases of cerebrovascular disease. All volunteers were in stable health, not suffering any acute illness, at the time of the study.

Partial purification of APP from plasma:

Blood (20–40ml) was drawn from fasting individuals within a 21-gauge needle into heparinized collection tubes and centrifuged at 2500 g for 15 minutes. The plasma supernatant fraction was separated from the blood cell pellet and centrifuged at 19,000 g for 25 minutes at 4° C. (J2-21 centrifuge, Beckman, USA) to remove any debris.

To detect APP by Western blotting, APP was partially purified from plasma by heparin-Sepharose chromatography. Plasma (2.5 ml) was loaded onto a 0.25 ml bed volume heparin-Sepharose (Pharmacia, Uppsala, Sweden) column (8 mm×5 mm) pre-equilibrated with buffer 1 (175 mM NaCl, 50 mM Tris-HCl, pH 7.4) at 4° C. The column was then washed with 3.25 ml buffer 1 and the APP eluted with 750 μl elution buffer (550 mM NaCl, 50 mM Tris-HCl, pH 7.4). Protein concentration was determined with BCA using bovine serum albumin standards (Pierce, Rockford, Ill., USA) according to the method of Smith et al (1985).

Washed platelets were prepared according to the method of Bush et al (1990). Platelets ($1.2 \times 10^7$) were solubilized in 30 μl of sample buffer COO mM Tris-HCl, 2% (w/v) sodium dodecyl sulfate (SDS), 0.01% (w/v) Bromophenol blue, 5% (v/v) β-mercaptoethanol (pH 6.8) and boiled for 10 minutes before Western blotting from polyacrylamide gels.

Plasma zinc assay:

$Zn^{2+}$ assays were performed by atomic absorption spectrophotometry according to the method in Davies et al. (1968).

Western bloting:

Western bloting procedures were as described by Bush et al (1990). Blots were probed with a mouse monoclonal antibody (mAb) 22C11 (Boehringer Mannheim, Munich, Germany), which recognises an epitope on the amino-terminus of APP (15), diluted 1:60,000 in blocking buffer. Plasma samples in this series of experiments were separated on 8.5% (w/v) polyacrylamide gels unless otherwise stated. Using these conditions, the 110 kDa APP immunoreactive band resolved into a doublet. However, for the purpose of the present analysis the sum of the signals generated by the doublet are regarded as belonging to the one 110 kDa region.

Reflectance analysis of blots:

Reflectance analysis of blots was carried out by video-capture with a Videk Megaplus camera (Kodak, Canandaigua, N.Y., USA) operated by PixelTools v1.1 (Perceptics, 1990). Quantitation was then performed with Image v1.29 software (W. Rasband, National Institutes of Health Research Services Branch, NIMH) which facilitated precise alignments of the individual blot lanes with the reflectance profile and the setting of exclusion limits of individual peaks in the four regions of interest at 130, 110, 65 and 42 kDa. The integrated reflectance (area under the curve) was thus computed for each of the four peaks in every sample. The values obtained were linear with concentration for each region over a range of plasma heparin-Sepharose eluate doses (20–90 μg of protein).

To compare the relative mounts of the four APP derivatives, the relative percentage of band signal to total lane signal was determined in each plasma sample and then averaged to give the values presented in Table 1. Independent samples Student's t-tests between pooled controls and Alzheimer's disease groups were performed for the four immunoreactive bands at a significance level of $p=0.0125$ (0.05 divided by the number of comparisons). Where those comparisons were significantly different, the test of simple effects (Weidemann et al, 1989) followed by Scheffe (1959) post hoc comparisons between all pairs of diagnostic groups (Alzheimer's disease, other neurological disease controls, normal young adult controls and non-demented age-matched controls) were then performed.

Assay of APP-degrading protease:

Aliquots (500 μl) of eluates from each heparin-Sepharose column were desalted using a 1.7 ml Sephadex G25 (Pharmacia, Uppsala, Sweden) column (8 mm×34 mm) equilibrated with 175 mM NaCl, 50 mM Tris-HCl, 1 mM $CaCl_2$, 1 mM $MgCl_2$, pH 7.4, in the presence or absence of 20 μM $ZnCl_2$ at 4° C., and the protein concentration adjusted to 0.80 mg/ml with the same buffer. The samples were then incubated at 37° for 2 hours, then an aliquot (81.3 μl) was removed, and the protein in each aliquot was precipitated with chloroform/methanol (Wessel and Flugge, 1984), boiled in SDS sample buffer and analysed by Western Noting using MAb 22C11.

The effects of inhibitors of various classes of proteases were assayed by adding them to these incubation mixtures and observing their influence upon the degradation of 130 kDa APP. A sample (500 μl) of a heparin-Sepharose eluate from the plasma of a normal young adult control was desalted into $Zn^{2+}$-buffer (175 mM NaCl, 50 mM Tris-HCl, 1 mM $CaCl_2$, 1 mM $MgCl_2$, 20 μM $ZnCl_2$, pH 7.4). Aliquots (containing 65 μg protein) were diluted to 0.80 mg/ml with the same buffer containing protease inhibitor, then incubated for 2 hours at 37° C. Protein was precipitated in each sample by the addition of chloroform/methanol (as above) and immunoblotted. The final concentrations of inhibitors in the incubation mixtures were EDTA (1 mM), diisopropyl fluorophosphate (DFP) (1 mM), aprotinin (10 μg/ml), N-ethylmaleimide (NEM) (1 mM), pepstatin A (10 μg/ml), al-antichymotrypsin (0.4 mg/ml) and soya bean trypsin inhibitor (SBTI) (1 mg/ml). The effects of $Al_3Cl$ (20 μM) and heparin (20 U/ml) were also measured in this system.

Brain APP preparation:

Amyloid protein precursor (APP) was purified according to the method in Moir et al. (1992). The preparations of purified 130 and 110 kDa APP were derived from human brain membrane extracts and contained the full-length APP with carboxyl terminus intact, but lacked the 17 residue signal peptide. The 130 and 110 kDa proteins were apparently in equal ratios on silver staining following polyacrylamide gel electrophoresis, and were fie only bands visible. The identity of these two proteins was confirmed by Western blots with monoclonal antibody (mAb) 22C11 (which recognises an amino terminal epitope on APP [Weidemann et at., 1989]), and by amino terminal sequencing. The protein concentration of the APP preparations was determined by amino acid analysis.

Human serum preparation:

40–60 ml of whole blood was allowed to clot for 3 hours in plain tubes at 20° C. The clotted blood was then incubated for 16 hours at 4° C., whereupon it was centrifuged at 1500 g for 15 minutes and the supernatant removed. The serum was further centrifuged at 1500 g for 15 minutes and the cell-free supernatant removed.

$^{65}Zn^{2+}$ binding to APP:

Binding analysis was performed as follows: Aliquots of APP (90 ng,≈1.1 pmole, assuming the average amino acid formula mass of APP is ≈80 kDa) were incubated at 20° C. Incubations (50 μl) were performed in 150 mM NaCl, 50 nM Tris-HCl, pH 7.4 in the presence of $10^6$ CPM of $^{65}Zn$ (175 nM). The incubation solution was then applied to a 1.1 ml bed volume Sephadex G25 (Pharmacia, Uppsala, Sweden) column pre-equilibrated with 150 mM NaCl, 50 mM Tris-HCl, pH 7.4 and allowed to settle before being desalted with 645 μl of the equilibration buffer. Previous analysis of the desalting properties of the column with mixtures of bovine serum albumin and potassium dichromate solution indicated that>95% of the protein in the incubation mixture would be desalted into this volume with no detectable free salt present. The deslated protein was collected directly into counting tubes containing 10 ml aqueous counting scintillant (ACSII, Amersham). Less than two minutes was required to complete the desalting. The amount of $^{65}Zn$ bound to desalted APP was determined by counting the collected sample in a beta-counter set to the broadest channel. Counting was determined to be 51% efficient. The binding of the labelled $Zn^+$ to APP was subjected to competition with unlabelled $Zn^{2+}$ and other metal chloride salts.

Characterisation of the putative zinc-binding domain of APP:

16 μg of the synthesized peptide GVEFVCCPLAEESDNVDSADAEEDDSDVWWGGAD, representing residues 181–214 of APP695 (or residues 181–200), or 16 μg of control peptide, was dissolved in 200 μl of blocking buffer (50 mM Tris-HCl, 1 mM $MnCl_2$ 10 mM β-mercaptoethanol, 20% methanol, pH 7.4) and dot-blotted onto PVDF (Immobilon-P, Millipore, Befored, Mass.) which had been pre-wetted with methanol. The blot was then incubated for 30 mins at 20° C. with 100,000 CPM of $^{65}Zn^{2+}$ in blocking buffer, in the presence or absence of various concentrations of competing unlabeled $Zn^{2+}$ or other divalent cations. After incubation the dot-blot was washed three times with 200 μl of blocking buffer without $MnCl_2$, the dot was excised and placed in 10 ml of scintillant and assayed by β-counting.

Iodination of APP:

100 kDa human brian full-length APP was iodinated by the Chloramine-T method. Iodinated APP ($^{125}I$-APP) was then separated from labelling reagents by Sephacryl G25 chromatography.

APP binding to heparin-Sepharose:

$^{125}I$-APP (0.37 pmol, 40,000 CPM) was loaded in 250 μl of buffer 1 (50 mM Tris-HCl, 0.1% BSA, pH 7.4±1 mM EDTA or 25–150 μM $ZnCl_2$) onto a 0.25 ml bed volume heparin-Sepharose column (8 mm×5 mm) pre-equilibrated with buffer 1 at 20° C. The column was then washed with 6 ml buffer 1 and the APP elated with aliquots of high-NaCl buffers. Gradient elations were performed by elating in 50 mM increments (700 μl) of the NaCl concentration from 0 to 1200 mM followed by a pulse of 2000 mM NaCl (in 50 mM Tris-HCl, 0.1% BSA, pH 7.4±1 mM EDTA or 50 μM $ZnCl_2$). Pulse elation of APP bound to heparin-Sepharose employed 700 μl of buffer 2 (50 mM NaCl, 50 mM Tris-HCl, 0.1% BSA, pH 7.4±1 mM EDTA or 25–150 μM $ZnCl_2$) followed by 700 μl of buffer 3 (100 mM CaCl, 50 mM Tris-Hcl, 0.1% BSA, pH 7.4±1 mM EDTA or 25–150 μM $ZnCl_2$), followed by 700 82 l of buffer 4 (500 mM NaCl, 50 mM Tris-HCl, 0.1% BSA, pH 7.4±1 mM EDTA or 50–150 μM $ZnCl_2$), followed by 2.5 ml of regenerating buffer (2000 mM NaCl).

APP binding to heparin-Sepharose was also studied using partially purified APP preparations derived from human brain membranes (according to the method of Moir et al, 1992) or from human serum. Washed brain membrane extract or human serum was adjusted to a NaCl concentration of 350 mM and applied to a Q-Sepharose column (5 cm×5 cm), washed with 350 mM NaCl, 50 mM Tris-Hcl, pH 7.4 (250 ml [×2 for brain membrane extract]) and elated with 1M NaCl 50 mM Tris-HCl, pH 7.4 (200 ml at 5 ml/min). This procedure causes an 80-fold enrichment of APP in the peak protein fractions, which are then pooled (Moir et at, 1992). The eluate (20 ml) was desalted into 25 mM Tris, pH 7.4 (30 ml) using a G25 Sephadex column (2.6 cm×40 cm). 15 ml of the product was adjusted to 50 μM $Zn^{2+}$ with 2 mM $ZnCl_2$, 50 mM Tris-Hcl, pH 7.4 and the other 15 ml was adjusted to the same volume with 50 mM Tris-HCl, pH 7.4. 10 ml of the deslated Q-Sepharose eluate, containing 6.7 mg protein, was applied to heparin-Sepharose (1.6 cm×5 cm) at 0.35 ml/min, washed with 100 ml of loading buffer, and elated by a 0 to 1500 mM NaCl gradient (±50 μM $Zn^{2+}$) in 52.5 ml at a flow rate of 0.35 ml/min. Fractions (1 ml) representing 20 mM NaCl increments were collected and 30 samples of each fraction were assayed for APP by Western blot with mAb 22C11 according to the method in Bush et at. (1990), modified by using PVDF membranes and by reducing the blocking time to 1 hour. The immunoreactive staining of the 1.30 kDa APP species seen on the blots was quantified by computer-assisted image capture reflectace densitometry (Bush et at., 1992). The 130 kDa reflectance signals on the blots were expressed as the ratio of the signal generated in one sample lane related to the 130 kDa APP reflectance reading of a sample of starting material present on every individual filter as an internal standard.

EXAMPLE 2

Abnormal profile of plasma APP in Alzheimer's disease:

A monoclonal antibody (22C11), which recognises the amino-terminus of APP (Weidemann et al, 1989) identified four major immunoreactive bands of APP (130, 110, 65 and 42 kDa) in western blots of human plasma (Bush et al, 1990; Buch et al, 1991). The relative abundance of these bands was surveyed in Alzheimer's disease and controls. The 130 kDa plasma APP band was increased and the 42 kDa plasma APP band was decreased in Alzheimer's disease cases compared to controls. The controls consisted of groups of non-demented age-matched persons (FIG. 1A), normal young adults (FIG. 1B) and other neurological disease patients. There was no consistent difference in the levels of the 110 and 65 kDa bands between Alzheimer's disease and controls. The total amount of APP immunoreactivity did not differ between Alzheimer's disease and control as the ratio of the total immunoreactivity of Alzheimer's disease: controls was 1.02±0.22 (mean±SD).

Quantitation of these findings by image capture analysis (Table 1) showed that the 130 kDa and 42 kDa bands in AD were significantly (two-tailed, $p<0.001$) increased and decreased, respectively, compared to pooled controls (averaged data from other neurological disease controls, normal young adult controls and non-demented age-matched controls). In Alzheimer's disease there was a 60% increase in the proportion of the 130 kDa form and a concomitant 35% decrease in the 42 kDa form. The immunoreactivity pattern was more evenly distributed in the pooled control group where the most concentrated APP immunoreactivity was in the 42 kDa region. This trend was maintained throughout the comparisons made of the Alzheimer's disease cases with the three control subgroups where post hoc analysis confirm the significance of the difference between the Alzheimer's disease and each control group in the 130 kDa region and between the Alzheimer's disease and young adult and elderly control groups in the 42 kDa region. There were no significant differences between the mean reflectance proportions of the three control groups in either the 130 or 42 kDa regions. The 110 kDa proportion was substantially higher and 65 kDa proportion substantially lower in the age-matched control group compared to the young adult control group.

Identification of the 110, 65 and 42 kDa plasma APP bands as possible cleavage products of the 130 kDa APP species:

When plasma APP from heparin-Sepharose eluates was incubated at 37° C. for 18 hours, the APP was slowly proteolytically degraded with a loss of the 130 kDa band and the accentuation of the three lower bands (110 kDa, 65 kDa and 42 kDa). Proteolysis was accelerated in the presence of $Zn^{2+}$. The zinc concentration required to stimulate proteolysis was 20 μm, which is within the range of the normal human plasma concentration (Davies et al 1968). The rate of $Zn^+$-enhanced proteolysis was similar in Alzheimer's disease compared to young adult control samples (FIG. 2), and identical degradation products were found in both groups. This indicated that the lower molecular weight APP forms in plasma could be degradation products of the 130 kDa form, and that proteolysis of the 130 kDa form in an Alzheimer's disease preparation changes the plasma APP profile towards that of control subjects.

$Zn^{2+}$-enhanced APP proteolysis of a young adult control preparation over two hours was completely inhibited both by EDTA, heparin and the serine protease inhibitors aprotinin, diisopropyl fluorophosphate, SBTI and, incompletely inhibited by $\alpha_1$-ACT. Neither $Al_3Cl$, the cysteine-protease inhibitor N-ethyl maleimide, nor the acid-protease inhibitor pepstatin A influenced the reaction.

Investigations of the origin of plasma APP forms:

The APP signal detected by Western bloting was unaffected by ultracentrifugation of plasma (100,000g×15 min). Plasma APP, as detected by MAb 22C11 on western blots of heparin-Sepharose eluates, could be immunoprecipitated by a rabbit antiserum raised against full-length native brain membrane-derived APP (90/3) and also by a rabbit antiserum raised against fusion protein $APP_{695}$ (anti-Fd-APP), but could not be immunoprecipitated by the preimmune serum of 90/3 or by rabbit antisera raised against synthetic peptides representing the carboxyl terminal 40 (anti-CT) or 100 (anti-A4CT) residues of APP. These data indicate that the APP forms observed in plasma are soluble and lack the carboxyl terminus.

To determine whether APP might be processed in whole plasma, fresh plasma from a young adult control was incubated at 37° C. over a period of eight days and the plasma APP assayed by heparin-Sepharose chromatography. No significant degradation of the 130 kDa APP form was observed over this time, indicating that constitutive processing of APP does not occur in plasma.

It has been previously reported that there is no difference between the content of APP in whole platelets or the electrophoretic pattern of platelet APP on Western blots in Alzheimer's disease cases compared to controls (Bush et al, 1990). Because other platelet abnormalities have been described in Alzheimer's disease (Zubenko et al, 1987), and also because APP is highly enriched in the platelet a-granule (Bush et al, 1990; Bush et al, 1991 and Cole et al, 1990), the possibility that platelet APP release contributes to the level of plasma APP was investigated. Platelets and plasma was examined from an individual with Fay platelet syndrome (GPS), a congenital abnormality where there are greatly diminished contents in the platelet a-granule. The GPS platelets contained<1% of the APP associated with normal platelets (FIG. 3). In contrast, the 130 kd plasma APP purified by heparin-Sepharose chromatography was approximately 50% reduced in GPS compared to the control (FIG. 3). These data indicate that the APP species seen in plasma are not likely to be an artefact caused by platelet release of APP during plasma preparation, but that platelet destruction, possibly in the spleen, may contribute a proportion of plasma APP.

EXAMPLE 3

Studies of the zinc modulation of APP physiology.

I) Effect of zinc loading upon human plasma APP.

100 mg elemental zinc (as sulphate, in capsules) was given orally to two individuals with Alzheimer's disease (NINCDS/ADRDC criteria with abnormal plasma APP profiles) and two age-matched controls (with normal plasma APP profiles). Zinc was continued for 7 days and morning fasting bloods collected before the commencement of zinc supplements and three weeks after ceasing the supplement. Western blots with monoclonal antibody 22C11 were carried out on 65 μg of plasma heparin-Sepharose eluate purified from the samples in the manner previously described. The results indicated an increase of 130 kDa species plasma APP relative to the other species present, in other words a shift towards the profile of APP species that is characteristic of Alzheimer's disease. The two control plasma APP profiles came to resemble Alzheimer's disease profiles and the two Alzheimer's profiles worsened. The proportional increase in the 130 kDa species was approximately 20% per day of zinc supplementation. An elderly control volunteer who was given a four-fold higher dose over three days demonstrated the same changes in his plasma APP profile which persisted for three days after ceasing supplementation.

II) Effect of lowering plasma zinc concentrations upon APP levels.

Post-prandial plasma zinc levels are known to fall≈10% in the hour after the meal. Seven Alzheimer's disease volunteers and six age-matched controls were assayed for plasma APP profile and zinc levels both fasting and one hour after a standardized breakfast. Both plasma zinc and 130 kDa APP levels fell by≈10% and there was a linear correlation between the change in APP level and the change in zinc concentration.

A young adult volunteer was given an oral dose of 50 g glucose while fasting. Both plasma zinc and 130, 110 and 65 kDa APP levels fell by≈10% within the first half hour after the glucose dose. Over a period of four hours with initial fall and subsequent rebound elevation in plasma zinc concentration was closely paralleled by plasma APP concentration as determined by APP radioimmunoassay using an antibody raised against native brain APP (90/3).

III) Measurement of plasma zinc concentrations in Alzheimer's disease.

Plasma zinc levels were shown not to be significantly elevated in fasting Alzheimer's disease plasma compared to age-matched controls.

IV) Effect of zinc loading upon rat brain APP.

16 week old Sprauge-Dawley male rats were injected daily for four days with 120 mg/kg $ZnCl_2$ solution. The animals were then anaesthetized, bled by intracardiac puncture and their brains removed; homogenized and separated into membrane and soluble fractions following ultracentrifugation. Western blots of heparin-Sepharose eluates of plasma, membrane extracts and soluble fractions revealed the development of a novel 80 kDa band in plasma and a 80% increase in the amounts of all forms of APP in the zinc-supplemented rats compared to control plasma and brain preparations (taken from litter-mates not receiving zinc).

V) Effect of extracellular zinc on cultured PC12 cells.

$10^6$ PC12 cells were plated for 24 hr in the presence of Dulbecco's modified Eagle's medium (DMEM, N2) supplemented with 8% fetal calf serum (FCS). The medium was then removed and replaced with DMEM±2 to 50 μM $ZnCl_2$ or another salt, and no FCS. Cells and media were harvested 48 hr later and aliquots of media, cell cytosol and membrane (following lysis and ultracentrifugation) were assayed for APP by Western blotting with mAb 22C11. The results of four experiments with duplicated samples revealed that the zinc induced a substantial increase in APP released into the media, ≈50% at 2 μM rising to a peak of≈200% at 50 μM. $FeCl_2$ had a similar effect and cuprous and aluminium chlorides had far smaller stimulatory effects. Smaller increases in cytosolic APP were seen accompanying these changes and there was no change in membrane associated APP levels.

VI) Effect of extracellular APP on zinc uptake by PC12 cells.

$10^6$ PC12 cells were plated for 24 hr in the presence of Dulbecco's modified Eagle's medium (DMEM, N2) supplemented with 8% fetal calf serum (FCS). The medium was then removed and replaced with DMEM with no FCS and incubated for a further 24 hr. The cells were then washed (×2 with DMEM) and incubated with DMEM supplemented with 10 nM 130/110 kDa purified brain membrane-associated APP carrying 20 000 CPM $^{65}Zn$ prepared as in FIG. 1 above. Following varying periods of incubation, the cells were harvested, washed, exposed to Pronase digestion to remove surface proteins and then lysed in scintillant and assayed in a beta-counter. The results indicated that≈10% of the counts were internalized in the presence of APP within an hour compared to≈4% in the absence of APP (two experiments with incubations performed in duplicate).

These data indicate that APP may play a role in the cellular uptake of external $Zn^{2+}$.

EXAMPLE 4

Binding of Zinc to APP

To determine whether APP binds zinc, incubations of human brain full-length APP with $^{65}Zn^{2+}$ and competing concentrations of unlabelled $Zn^{2+}$ were performed. Maximal binding was observed at 15 minutes (30% $B_{max}$ at 1 minute) which was saturable at a dissociation constant (KD) of 764 nM at pH 7.4, and 2.08 μM at pH 6.4. The binding of $^{65}Zn^{2+}$ to APP was specific for all competing metal ions, including $Ca^{2+}$ and $Mg^{2+}$, with $Co^{2+}$ the most competitive cation, able to compete off 70% of $B_{max}$ at 20 μM. Heavy metals, $Cu^{2+}$ and $Al^{3+}$ were able to compete off≈60% of $B_{max}$ at 20 μM. The stoichiometry of $Zn^{2+}$-binding at APP was 1:1.

A putative $Zn^{2+}$ binding site was identified by trypsin digestion of APP followed by amino-terminal sequencing of a 6 kDa digestion fragment which bound to $Zn^{2+}$-charged chelating-Sepharose. The fragment sequence was FRGVEFVXXPLA. To further characterise and confirm the $Zn^{2+}$-binding properties of this region of APP, candidate synthetic peptides were studied by dot blot. A synthetic peptide representing residues 181–214 of APP was able to bind $Zn^{2+}$ in a saturable and specific manner. The role of the cysteine residues in contributing to this peptide's ability to bind $^{65}Zn^{2+}$ was determined by studying the ability of the same peptide to bind $^{65}Zn^{2+}$ where the cysteines in the peptide had been modified by carboxyamidomethylation, and by studying $^{65}Zn^{2+}$ binding to another synthetic peptide representing residues 189–220 of APP695, lacking the cysteine residues at positions 186/187. Both of these peptides were able to bind $^{65}Zn^{2+}$ significantly above background, but to only approximately 15% of the amount of $^{65}Zn^{2+}$ binding that occurred using the same quantity of 181–214 peptide (or 181 to 200), indicating that the cysteine residues are obligatory for the zinc-binding properties of this peptide. Similar quantities of other peptides representing other regions of the APP molecule (residues 422–433, 581–601, 645–655) and other control peptides (renin and Insulin A chain) were unable to bind $Zn^{2+}$, whereas the positive control (Insulin B chain) bound $^{65}Zn^{2+}$.

To explore the functional significance of $Zn^{2+}$ binding to APP, the effect of $Zn^{2+}$ on heparin binding to APP derived from three sources; iodinated purified brain APP, partially purified unlabelled human brain APP, and partially purified unlabelled human serum APP, were studied. The mount of brain APP binding to heparin was increased≈50% by the presence of 50 μM $Zn^{2+}$ specifically. The increase in $^{125}I$-APP binding to heparin reached a plateau at 75 μM $Zn^{2+}$. $Zn^+$ increased the proportion of higher-affinity binding of APP to heparin, increasing the mount of $^{125}I$-APP that was recovered from the 50–2000 mM NaCl elution fraction by approximately 3-fold in the present of 50 μM $Zn^{2+}$ and by 4.5-fold in the presence of 100 μM $Zn^{2+}$. $Ca^{2+}$ and $Mg^{2+}$ did not alter the profile of $^{125}I$-APP elution, $Co^{2+}$ at 75 μM increased the recovery of $^{125}I$-APP in the 100–500 and 500–2000 mM NaCl fractions, and $Al^{3+}$ decreased the recovery of $^{125}I$-APP except in the 500–2000 mM NaCl fraction where recovery was increased approximately 4.5-fold. $Zn^{2+}$ at 50 μM had a similar effect on the NaCl gradient elution profile of partially purified brain APP bound to heparin-Sepharose. The presence of $Zn^{2+}$ caused an increase in the amount of APP recovered in all fractions from 1110 to 1644 reflectance units, an increase of 48%, and also caused an increase in APP recovery in fractions eluted by NaCl concentrations above 520 mM. Despite the increase in APP recovery in the eluted fractions, protein assay showed a 13% reduction in the amount of eluted protein, indicating that the presence of $Zn^{2+}$ increased the specificity of APP binding to heparin. $^{125}$I-APP recovery occurred over a range of NaCl concentrations 200–300 mM lower than partially purified brain APP elution. This may be the result of radiolytic or oxidative damage to the APP molecule during iodination, although the possibility that the elution of partially purified APP is influenced by co-purified material cannot yet be excluded.

The presence of 50 μm $Zn^{2+}$ promoted a smaller increase in the binding of partially purified serum APP to heparin-Sepharose. In serum samples, the increase in APP recovered from the NaCl elation was≈10%, however protein assay of recovered fractions indicated that, unlike the effect of $Zn^{2+}$ upon heparin-Sepharose chromatography of partially purified brain proteins, the effect of $Zn^{2+}$ upon the heparin-Sepharose chromatography of partially purified serum was to increase the amount of protein recovered by 12%. Unlike its effect on the brain-derived APP salt elation profile, the presence of $Zn^{2+}$ in the heparin-Sepharose chromatography of serum-derived APP did not increase the proportion of higher-affinity binding.

The effect of $Zn^{2+}$ in modulating heparin binding to APP was also studied in a Biosensor system. At 100 μM, $Zn^{2+}$ was shown to strongly promote heparin binding to APP purified from rat brain. This effect was most pronounced and most specific for $Zn^{2+}$, as opposed to the absence of divalent cations or the presence of $Ca^{2+}$, $Mg^{2+}$ or $Co^{2+}$, and was most evident when the heparin:APP ratio was low. Concentrations of $Zn^{2+}$ as low as 50 nM had a marked effect on increasing heparin binding to rat brain APP. $Zn^+$ at 50 nM promoted a≈170% increase in heparin binding, the effect saturating at 70

EXAMPLE 5

Heparin Protects APP from Proteolytic Cleavage Zinc Abolishes the Protective Effect of Heparin The proteolytic activity of trypsin (Boehringer, Mannheim) was studied to determine whether it was modulated by a range of doses of heparin (Sigma) and $ZnCl_2$. Both heparin and $ZnCl_2$ left tryptic activity unaltered as measured by its ability to cleave a fluorogenic synthetic substance Z-F-R-AMC, indicating that trypsin is a suitable serine protease to employ in studies of the modulation of APP proteolytic resistivity by heparin and zinc. Digestions of human brain membrane-derived APP (which contains the intact carboxyl terminus) were carried out with trypsin in an amount ratio of 1:64 (enzyme:substrate) for one hour at 37° C. Western blots for APP using the APP binding monoclonal antibody 22C11 were used to monitor the profession of the proteolytic reaction and to detect breakdown products. It was found that the presence of heparin in concentrations as low as 100 nM caused a marked reduction in the rate of degree of brain APP degradation by trypsin. This protective effect saturated at 10 μM. The presence of $Zn^{2+}$ (up to 100 μM) or EDTA (1 mM) had no effect on the rate of APP proteolysis by trypsin in this reaction. However, the presence of $Zn^{2+}$ (above 1 μM) with heparin (1 μM) in the proteolytic reaction completely abolished the protective effect of heparin. This was an unexpected response given that previous results showed that the presence of $Zn^{2+}$ promotes heparin binding to APP.

One possible explanation for this finding is that zinc binding to APP could promote heparin binding at a different site on the protein, known to be towards the center of APP, by enhancing the protein's conformational stability. The conformational stabilisation caused by zinc may promote the central region of APP to remain open to heparin attachment to residues 98 to 105 of $APP_{695}$ (CKRGRKQCKTH) or residues 318 to 331 of $APP_{695}$ (KAKERLEAKHRER), perhaps by a charge effect. When heparin binding occurs in the absence of zinc, the protein may be induced to assume a more globular and protease-resistant conformation. This zinc binding to APP could stabilise the APP to the extent that heparin binding is prevented from inducing the alteration in APP conformation which increases protease resistivity.

EXAMPLE 6

Administration of Zinc in Alzheimer's Disease (AD)

The subjects from Example 3 were studied. The healthy volunteers suffered no ill effects from the zinc supplementation. The two AID volunteers because acutely unwell while on zinc supplementation.

They both suffered a severe loss of cognitive function with mini-mental state examination (Folstein et al., 1975) scores deteriorating from moderately demented levels to unrecordable. Eye movement abnormalities and general levels of self care worsened over the period of supplementation. This response was consistent with a neurotoxic response to the zinc supplementation. When zinc supplementation was ceased, cognitive function returned to the previous levels within two weeks.

Accordingly, a diagnostic test may involve an oral zinc challenge. A clinically measured neurotoxic response would be compatible with a diagnosis of AID.

The interaction between APP, zinc and heparin is currently not well understood, although from the description herein it is clear that both zinc and heparin interact with APP through specific binding sites modulating its stability to proteolysis. The inventors have identified a zinc binding site and a heparin binding site on APP. There may be additional zinc and heparin binding sites on the APP molecule which modulate its stability. This invention extends to modulating the interaction of zinc and/or heparin and/or other agents with APP to treat, ameliorate or prevent Alzheimer's disease and other neurological disorders associated with aberrant processing of APP.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Table 1. Ratios of plasma APP forms analysed by image capture in Alzheimer's disease and controls.

Heparin-Sepharose eluates of Alzheimer's disease and control plasma samples were immunoblotted with MAb 22C11 and the reflectances of the bands at 130, 110, 65 and 42 kDa were measured by computer-assisted image capture analysis (see Example 1). The relative mounts of the four APP derivatives, as percentages of total lane signal, were determined in each plasma sample and averaged to give the values presented here. Independent samples t-tests between pooled controls and Alzheimer's disease groups were performed in the four regions at a significance level of 0.0125. Comparisons were significant for only two regions, 130 and 42 kDa (two-tailed, $p<0.001$). Comparisons between all pairs of diagnostic groups (Alzheimer's disease, other neurological disease controls, normal young adult controls and non-demented age-matched controls) were then performed for the 130 and 42 kDa bands (see Example 1).

TABLE 1

| | Mean age ± SD | Percentage of Total APP ± SD | | | |
| --- | --- | --- | --- | --- | --- |
| | | 130 kDa | 110 kDa | 65 kDa | 42 kDa |
| AD, n = 27 | 64.8 ± 6.4 | 37.5 ± 11.0 | 23.2 ± 5.7 | 21.9 ± 8.0 | 17.3 ± 6.8 |
| Pooled controls, n = 34 | 52.2 ± 16.7 | 22.8 ± 6.3 *** | 24.7 ± 7.1 NS | 26.4 ± 7.4 NS | 26.5 ± 8.9 *** |
| Neurological controls, n = 6 | 64.0 ± 6.8 | 25.0 ± 8.3 * | 22.7 ± 5.8 | 31.0 ± 3.2 | 21.3 ± 10.6 NS |
| Age-matched controls, n = 15 | 64.5 ± 3.8 | 20.1 ± 5.1 | 30.1 ± 5.0 | 21.0 ± 4.0 | 28.8 ± 7.2 * |
| Young adult controls, n = 13 | 32.5 ± 6.9 | 24.8 ± 5.9 | 18.5 ± 4.1 | 30.5 ± 7.9 | 26.2 ± 9.3 |

*** t-test, p < 0.001
* Scheffe, p <0.05
NS No significance

REFERENCES:

Bush. A. I., Martins, R. N., Rumble, B. et al, *J. Biol. Chem.* 265: 15977-15933, 1990.

Bush. A. I., Beyreuther, K., Masters, C. L. Chapter 70 in K. Iqbal, DRC McLachlan, W. Winblad, H. M. Wisniewski. (eds.), *Alzheimer's Disease: Basic Mechanisms, Diagnosis and Therapeutic Strategies.*, John Wiley and Sons, Chichester, 1991.

Bush. A. I., et al, *Anals. of Neurology* 32: 57-65, 1992.

Cole G. M., Galasko D, Shapiro I. P., Saitoh t. *Biochem Biophys Res Comm* 170: 288-295, 1990.

Davies, L. et al. *Neurology* 38: 1688-1693, 1988.

Davies IJT, Musa M, Dormandy T. L. *J Clin Path* 21: 359-365, 1968.

Esch, F. S. et al. *Science* 248: 1122-1124, 1990.

Folstein M. F., Folstein S. E., McHugh P. R. *Mini-mental state: a practical method for grading the cognitive state of patients for the clinician. J. Psych. Res.* 15: 189-198, 1975.

Folstein M. F., Folstein S. E., McHugh P. R. *J Psych Res* 12: 189-198, 1975

Goldgaber, D., Lerman, M. I., McBride, O. W., Saffiotti, U. and Gajdusek, D. C. *Science* 235: 887-880, 1987.

Hilder R. C., et al. *Biochem. Pharmac.* 39: 1005-1012, 1990.

Kang. J. et. al. *Nature* 325: 733-736, 1987.

McKhann G, Drachman D, Flostein M, Katzman R, Price D, Stadlan E. M. *Neurology* 34: 939-944, 1984.

Moir et al. *J. Neurochem.* 1490-1498, 1992.

Mönning U, König G, Prior R, et al. *FEBS Letters,* 277: 261-266, 1990.

Multhaup G, Mechler H, Masters C. L., Beyreuther K. $\beta A4$ *amyloid protein procursor of Alzheimer's disease interaction with heparin: Identification of a heparin binding domain.* (in preparation).

Palmert, M. R. et al. *Proc. Natl. Acad. Sci. USA* 86: 6338-6342, 1989.

Podlisny M. B., Mammen A. L., Schlossmacher M. G., Palmert M. R., Younkin S. G., Selkoe D. J. Biochem Biophys Res Comm 167: 1094-1101, 1990.

Rosa J-P, George J. N., Bainton D. F., et al *J Clin Invest* 80: 1138-1146, 1987.

Rumble B., Retallack R., Hilbich C. et al. *N. Engl. J. Med,* 320: 1446-1452, 1989.

Scheffé H. Wiley, New York 1959.

Sisodia, S. S., Koo, E. H., Beyreuther, K., Unterbeck, A. and Price, D. L. *Science* 248: 492-495, 1990.

Smith P. K., Krohn R. I., Hermanson G. T., et al, *Anal Biochem* 150: 76-75, 1985.

Stanton R. *Dietary sources of essential minerals.* 15: 36-38, (1992).

Weidemann A, König G, Bunke D, et al *Cell* 57: 114-126, 1989.

Wessel D, Flügge U. I. *Anal biochem* 138: 141-143, 1984.

Zubenko G. S., Cohen B. M., Boiler F, Malinakova I, Keffe N, Chojnacki B. *Ann. Neurol* 22: 237-244, 1987.

We claim:

1. A method of assaying for probable Alzheimer's disease in a human which comprises determining in a sample of human circulatory fluid the amount of at least one of the 130 kDa form or 42 kDa form of amyloid precursor protein (APP) in said sample, wherein said APP is detected by Western blot with antibodies specific for at least one of the 130 kDa form or 42 kDa form of APP, comparing the levels of at least one of the 42 kDa form or the 130 kDa form in said sample to a normal control and correlating a significant increase in the 130 kDa form or a significant decrease in the 42 kDa form with the presence of Alzheimer's disease, wherein said 130 kDa form and 42 kDa form specifically binds to antibody 22C11.

2. The method according to claim 1 wherein the circulatory fluid is obtained after the human has undergone at least four hours of fasting.

3. The method according to claim 1 wherein the circulatory fluid is blood plasma.

* * * * *

UNITED STATES PATENT AND TRADEMARK OFFICE
CERTIFICATE OF CORRECTION

PATENT NO.      : 5,705,401
DATED           : January 6, 1998
INVENTOR(S)     : Colin L. Masters et al.

It is certified that error appears in the above-identified patent and that said Letters Patent is hereby corrected as shown below:

Column 3,
Line 63, ".cations" should read -- cations --

Column 6,
Line 5, after "zinc" delete "."

Column 7,
Line 11, "fight" should read -- right --
Line 61, "$\mu$" should read -- $\mu l$ --

Column 9,
Line 34, "menial" should read -- mental --
Line 64, "COO" should read -- 100 --

Column 10,
Line 58, "Noting" should read -- bloting --

Column 11,
Line 7, "al" should read -- $\alpha 1$ --
Line 18, "fie" should read -- the --
Line 22, "at." should read -- al. --
Line 54, "Zn $^+$" should read -- Zn $^{2+}$ --

Column 12,
Line 26, "82" should read -- $\mu l$ --
Line 33, "elated" should read -- eluted --
Line 51, after "30" insert -- $\mu l$ --
Line 58, "at." should read -- al. --

Column 13,
Line 17, "AID" should read -- AD --
Line 50, "Zn +" should read -- Zn $^{2+}$ --

Column 14,
Lines 25 and 31, "a-granule" should read -- -granule --
Line 29, "Fay" should read -- gray --

Column 15,
Line 31, "80%" should read -- $\approx$ 80% --

UNITED STATES PATENT AND TRADEMARK OFFICE
CERTIFICATE OF CORRECTION

PATENT NO. : 5,705,401
DATED : January 6, 1998
INVENTOR(S) : Colin L. Masters et al.

It is certified that error appears in the above-identified patent and that said Letters Patent is hereby corrected as shown below:

Column 16,
Line 31, "APP695" should read -- $APP_{695}$ --
Line 46, "mount" should read -- amount --
Line 50, "$Zn^+$" should read -- $Zn^{2+}$ --

Column 17,
Line 31, "70" should read -- 70 $\mu$M. --
Line 48, "profession" should read -- progression --
Line 53, "The presence..." should begin a new paragraph.
Line 59, "$Zn^+$" should read -- $Zn^{2+}$ --

Column 18,
Lines 16 and 28, "AID" should read -- AD --

Signed and Sealed this

Eleventh Day of March, 2003

JAMES E. ROGAN
*Director of the United States Patent and Trademark Office*